US012675074B2

(12) United States Patent
Knüttel

(10) Patent No.: US 12,675,074 B2
(45) Date of Patent: Jul. 7, 2026

(54) OPTICAL SYSTEM FOR DIGITAL HOLOGRAPHY

(71) Applicant: AKMIRA OPTRONICS GMBH, Potsdam (DE)

(72) Inventor: Alexander Knüttel, Potsdam (DE)

(73) Assignee: AKMIRA OPTRONICS GMBH, Potsdam (DE)

( * ) Notice: Subject to any disclaimer, the term of this patent is extended or adjusted under 35 U.S.C. 154(b) by 0 days.

(21) Appl. No.: 18/869,868

(22) PCT Filed: Jun. 2, 2023

(86) PCT No.: PCT/EP2023/064867
§ 371 (c)(1),
(2) Date: Nov. 27, 2024

(87) PCT Pub. No.: WO2023/233016
PCT Pub. Date: Dec. 7, 2023

(65) Prior Publication Data
US 2025/0334926 A1 Oct. 30, 2025

(30) Foreign Application Priority Data
Jun. 3, 2022 (DE) ..................... 10 2022 114 150.0

(51) Int. Cl.
*G03H 1/04* (2006.01)
*G03H 1/02* (2006.01)
*A61B 1/00* (2006.01)
(52) U.S. Cl.
CPC ......... *G03H 1/0443* (2013.01); *G03H 1/0248* (2013.01); *A61B 1/00194* (2022.02);
(Continued)

(58) Field of Classification Search
CPC ............... G03H 1/0443; G03H 1/0248; G03H 2001/0452; G03H 2222/12;
(Continued)

(56) References Cited

U.S. PATENT DOCUMENTS 6,525,846 B1 * 2/2003 Yan et al. ................. G02B 5/32
359/15
7,466,421 B2 * 12/2008 Weitzel .................... G01B 9/02
356/451

(Continued)

FOREIGN PATENT DOCUMENTS

DE 69815361 4/2004
DE 69815361 T2 * 4/2004 ............. G02B 27/10
DE 102015113465 2/2017

*Primary Examiner* — William C Vaughn, Jr.
(74) *Attorney, Agent, or Firm* — JMB Davis Ben-David

(57) ABSTRACT

The invention relates to an optical system (1) comprising at least the following components: a first holography arrangement (2) comprising a first diffraction element (3) which is formed by a first prism arrangement (4) having at least a quadrangular base surface, wherein a lateral surface of the first prism arrangement (4) has the following lateral surface regions: a first entrance surface (31) for reference light (100) extending along a first entrance plane (310), a second entrance surface (32) for object light (200) extending along a second entrance plane (320), wherein the first and second entrance surfaces (31, 32) form opposite lateral surface regions of the first prism arrangement (4), an exit surface (33) which extends along an exit plane (330) and through which diffracted reference light (102) and diffracted object light (201) can exit from the first diffraction element (3), a prism surface (34), opposite to the exit surface (33), extending along a prism plane (340), an optical transmission diffraction grating arrangement (36) which is arranged in the first diffraction element (3) and extends along a diffraction plane (360), which intersects the first entrance plane (310),
(Continued)

between the first entrance surface (31) and the exit surface (33), wherein the transmission diffraction grating arrangement (36) of the first diffraction element (3) comprises at least one first volume phase hologram grating, and in that the first holography arrangement (2) has, on the side of the prism surface (34), a first mirror (35) having a first mirror plane (350), wherein the first mirror plane (350) encloses an angle $\alpha$ with the diffraction plane (360) and the prism plane (340) encloses an angle $\omega_2$ with the diffraction plane (360), wherein at least one of the angles $\alpha$, $\omega_2$ is different from 45°.

15 Claims, 6 Drawing Sheets

(52) U.S. Cl.
CPC . *G03H 2001/0452* (2013.01); *G03H 2222/12* (2013.01); *G03H 2222/13* (2013.01); *G03H 2223/18* (2013.01); *G03H 2223/23* (2013.01); *G03H 2223/24* (2013.01)

(58) Field of Classification Search
CPC .......... G03H 2222/13; G03H 2223/18; G03H 2223/23; G03H 2223/24; A61B 1/00194
USPC ........................................................ 348/40
See application file for complete search history.

(56) References Cited

U.S. PATENT DOCUMENTS

| | | | | |
|---|---|---|---|---|
| 2004/0070853 | A1* | 4/2004 | Ebizuka et al. ......... | G02B 5/04 |
| | | | | 359/833 |
| 2005/0243421 | A1* | 11/2005 | Arns ........................ | G02B 5/18 |
| | | | | 359/558 |
| 2013/0077140 | A1* | 3/2013 | Bach .................. | G02B 27/0103 |
| | | | | 359/15 |
| 2014/0177782 | A1* | 6/2014 | Herold .................... | A61B 6/06 |
| | | | | 378/4 |
| 2021/0063137 | A1* | 3/2021 | Gao et al. .......... | G01B 9/02045 |
| 2022/0034791 | A1* | 2/2022 | Zhang ................. | G01N 11/211 |

* cited by examiner

OPTICAL SYSTEM FOR DIGITAL HOLOGRAPHY

CROSS-REFERENCE TO RELATED APPLICATIONS

This is the U.S. National Stage of International Patent Application No. PCT/EP2023/064867 filed Jun. 2, 2023, which was published in German under PCT Article 21(2), and which in turn claims the benefit of German Patent Application No. DE 10 2022 114 150.0 filed Jun. 3, 2022.

The invention relates to an optical system for digital holography, in particular for use in the field of minimally invasive medicine.

From the prior art, so-called GRISMs are known as optical components that consist of a combination of an optical grating and a prism (from English: GRating+PRISM). In a GRISM, light of the central wavelength propagates straight through the GRISM, and the light still splits spectrally. This makes it particularly easy to construct a spectral imaging device.

In addition, various systems are known in the field of digital holography in which a coherent reference light beam is superimposed on a coherent object light beam, wherein the spatial structure of a surface of an object from which the object light was reflected or backscattered before it was superimposed on the reference light can be calculated from the interference pattern of the superposition. For this purpose, such systems have a camera that is configured to record the interference pattern. A laser is typically used as the source for the reference light and the object light, the laser light of which is split into the reference light beam and the object light beam by means of a beam splitter. This ensures the spatial and temporal coherence of reference light and object light. Systems of this type are preferably used in 3D endoscopic imaging procedures in the field of minimally invasive medicine.

Based on the known prior art, an improved system is to be created that enables multi-spectral digital holography, in particular in the field of minimally invasive medical technology.

This object is achieved by an optical system that comprises at least the following components:

A first holography arrangement comprising a first diffraction element which is formed by a first prism arrangement having a quadrangular base surface, wherein a lateral surface of the first prism arrangement has the following lateral surface regions:

a) a first, in particular planar, entrance surface for reference light, which extends along a first entrance plane, wherein the first entrance surface can be part of a first end face, and b) a second, in particular planar, entrance surface for object light, which extends along a second entrance plane, wherein the first and the second entrance surface form opposite lateral surface regions of the first prism arrangement, wherein the second entrance surface can be part of a second end face, c) an exit surface, which is planar in particular and extends along an exit plane and through which diffracted reference light and diffracted object light can exit from the first diffraction element, d) a prism surface opposite to the exit surface, e) an optical transmission diffraction grating arrangement which is arranged in the first diffraction element and extends along a diffraction plane, which intersects the first entrance plane and the exit plane, between the first entrance surface and in particular the exit surface, in particular so that the transmission diffraction grating arrangement forms a triangular prism with the first entrance surface and the exit surface.

The invention furthermore provides that the transmission diffraction grating arrangement of the first diffraction element comprises at least one first volume phase hologram grating, and that the first holography arrangement has a first, in particular planar, mirror having a first mirror plane on the side of the prism surface of the first diffraction element, wherein the first mirror plane encloses an angle $\alpha$ with the diffraction plane, and the prism surface encloses an angle $\omega_2$ with the diffraction plane, wherein at least one or both angles $\alpha$, $\omega_2$ is/are not equal to 45°, in particular deviate from 45° by more than $\pm 0.2°$, in particular wherein the angle $\alpha=45°\pm\beta$ with $\beta>0°$, in particular wherein the angle $\omega_2=45°\pm\rho_2$ with $\rho_2>0°$, in particular in order to achieve a maximum possible efficiency for object and reference light in the first holography arrangement.

Preferably, $\beta$ and/or $\rho_2$ are greater than 0.2.

Preferably, $\beta$ and/or $\rho_2$ are less than 20°.

According to the invention, the angles $\beta$ and $\rho_2$ are in particular selected such that reference light incident on the transmission diffraction grating arrangement at an angle of 45° is diffracted by the transmission diffraction grating arrangement in the direction of the prism surface and is reflected by the first mirror in such a way that the reflected reference light, due to an angle of incidence of the reflected reference light on the transmission diffraction grating arrangement, is diffracted again in the direction of the first entrance surface to a lesser extent, in particular a proportion that is less by at least 30%, than the reference light originally incident on the transmission diffraction grating arrangement from the side of the first entrance surface, and a remaining proportion of the reflected reference light propagates through the transmission diffraction grating arrangement in the direction of the exit surface.

The terms 'reference light' and 'object light' are known from the prior art in connection with digital holography. The reference light is superimposed in the diffraction element with the object light returned (e.g., reflected or scattered) from the object, which in particular originates from the same coherent light source as the reference light, so that after further propagation an interference pattern arises near the exit surface on an array detector, such as a 2D sensor or a camera. In particular, this pattern contains the complete wave information about the object light, so that the object can be calculated in the form of a hologram from the interference pattern. In particular, depth information, i.e. 3D information about the object, can be generated in this way, especially when a large number of wavelengths, for example in the form of spectral lines, are used for the reference light and object light.

The invention can therefore be combined particularly well in connection with minimally invasive medical imaging instruments, which are to be designed to generate 3D information from the field of view of the instrument. Stereoscopic optics are too large for minimally invasive use, which makes digital holography of great utility in this field of technology.

In the state according to the invention, it is provided in particular that reference light enters the diffraction element via the first entrance surface, in particular in a collimated manner. There it is diffracted by the transmission diffraction grid arrangement in the direction of the prism surface. The mirror reflects the diffracted reference light back in the direction of the transmission diffraction grating arrangement—but at an angle that can be calculated from Snell's law; due to the angle, at least part of the reflected reference light is not diffracted by the transmission diffraction grating arrangement, but is transmitted and propagated in the direction of the exit surface. According to the invention, the first object light enters the diffraction element via the second entrance surface and is diffracted by the transmission diffraction grating arrangement directly in the direction of the exit surface, where it is superimposed and in particular interferes with the reference light on an array detector or camera chip.

The invention provides an optical system for digital holography which makes it possible to separate multiple wavelengths comprised in the reference light, in particular wherein the wavelengths are present in the form of spectrally spaced-apart spectral lines, from a comparatively large wavelength range on the side of the exit surface, and which at the same time is impressive due to an extremely compact and robust design.

In particular, the optical properties of a volume phase hologram grating are combined in an extremely advantageous manner with a first mirror that is advantageously inclined in relation to the transmission diffraction grating arrangement, which makes it possible for the first time to resolve the bandwidth of wavelengths.

By way of the first mirror arranged according to the invention, later image information obtained from the object light superimposed on the reference light at the exit surface can be shifted outside the typically interfering DC range.

Furthermore, the first mirror ensures that the part of the reference light reflected at the first mirror is only attenuated slightly—or not at all—by the transmission diffraction grating arrangement when passing through the first transmission diffraction grating arrangement. If the angles $\beta$ and $\rho_2$ were equal to 0°, then a very large part of the reference light would be diffracted back to the first entrance surface by the transmission diffraction grating arrangement and thus would not reach the exit surface.

The first mirror comprises a first mirror plane extending along a reflective layer of the first mirror, in particular wherein the first mirror consists of the reflective layer.

In the following, an angle of the first mirror with respect to a surface or a plane always means the angle of the first mirror plane of the first mirror with the surface or the corresponding plane.

The term 'prism' in the context of this invention refers in particular to a geometric, in particular physical body, which has two opposing base surfaces which are connected to one another via lateral surface regions of a lateral surface arranged at the edges of the base surfaces.

According to the invention, the base surface of the prism arrangement is at least quadrangular, i.e. the base surface has a polygon, wherein the polygon has at least four corners. However, it is entirely possible and conceivable that the base surface comprises further corners and thus further lateral surface regions, which are designed for other purposes, for example, are comprised by the prism arrangement.

A quadrangular prism therefore has four lateral surface regions that delimit two quadrangular base surfaces. Unless otherwise defined, the base surfaces have an identical shape and size.

The term 'prism arrangement' in the context of the present invention refers in particular to a fixed arrangement of at least one prism or multiple prisms.

According to one embodiment of the invention, the at least quadrangular prism arrangement is integrally or monolithically formed.

The terms 'integrally designed' or 'integrally formed' are to be understood as synonymous with 'monolithic' in the context of the invention.

According to one embodiment of the invention, the at least quadrangular prism arrangement is formed by a first and a second triangular prism, wherein the two triangular prisms are connected to one another along the diffraction plane via the transmission diffraction grating arrangement. The first triangular prism of the two triangular prisms comprises in particular the first entrance surface, the exit surface. The second triangular prism of the two triangular prisms comprises in particular the second entrance surface, the prism surface. In particular, the quadrangular prism arrangement is formed from two separate triangular prisms that are firmly connected to one another.

In general, the at least quadrangular prism arrangement can be embodied monolithically in any embodiment of the invention-unless explicitly disclosed otherwise. Alternatively, the at least quadrangular prism arrangement can be formed in an analogous manner by various prisms connected to one another.

If no information is given about the composition and/or nature of the prism arrangement, this comprises both the monolithic design and embodiments in which the prism arrangement is formed, for example, by a plurality of separate prisms connected to one another.

In particular, all lateral surface regions of the at least quadrangular prism arrangement are planar.

According to one embodiment of the invention, the prism arrangement comprises a solid transparent body, which in particular comprises a transparent glass or polymer.

According to one embodiment of the invention, the prism arrangement, in particular with the exception of the transmission diffraction grating arrangement, consists of a transparent glass and/or polymer.

According to one embodiment of the invention, the first mirror has a reflectance between 10% and 100%, in particular greater than 70%. The reflection level can be up to nearly 100%, for example 95% or even 99%.

Since there is typically sufficient reference light available (in comparison to the object light), the reflectance of the first mirror does not have to be particularly high.

In particular, the first mirror has a smoothness equal to or better than $\lambda/2$.

According to a further embodiment of the invention, the transmission diffraction grating arrangement is a substantially planar transmission diffraction grating arrangement.

Volume Phase Holographic (Transmission) Gratings (abbreviated VPH) are known from the prior art. The volume phase hologram grating is in particular a transmission grating. Volume phase hologram gratings consist, for example, of a film of dichromized/dichromatic gelatin (DCG) between two glass substrates, in particular wherein the glass substrates are formed by the first and the second triangular prism, in particular wherein the gelatin is arranged between lateral surface regions of the first and the second triangular prism, which extend along the diffraction plane. Volume phase hologram gratings offer high first order diffraction peak efficiency and uniform performance over a specified bandwidth.

As an alternative to gelatin, a photopolymer can also be used, which is formed into a volume phase hologram grating by appropriate exposure. In particular, the photopolymer can be introduced between the two glass substrates after exposure. Photopolymers have the advantage over gelatin of not being viscous and therefore easier to handle. For both gelatin and photopolymers, layer thicknesses for the volume phase hologram grating in the order of magnitude of a few micrometers up to approximately 100 μm are possible.

Furthermore, volume phase hologram gratings are also known which are introduced into glass and in particular do not include any gelatin.

Volume phase hologram gratings in PTR glass have the advantage over other volume phase hologram gratings made of gelatin or photopolymer that they are more thermally stable, since these are typical properties of glass. However, since the refractive index modulations in PTR glass are approximately an order of magnitude weaker than in gelatin and photopolymers, the active glass layer has to be correspondingly thicker. However, this results in restrictions in the angle dispersion or in the spectral characteristics. This means that depending on the requirements for the diffraction element, an appropriate volume phase hologram grating material and production method can be selected.

In particular, the first holography arrangement is configured and formed to be operated in a so-called "Littrow arrangement". The diffraction element and thus the first holography arrangement is arranged in the system in such a way that the diffraction plane encloses an angle of 45° with an optical axis of the diffraction element and thus the first mirror plane encloses the angle β and/or the prism surface encloses an angle $\rho_2$ with the optical axis. As a result, the reference light entering the first diffraction element via the first entrance surface, which initially propagates along the optical axis, is ideally diffracted by the transmission diffraction grating arrangement by a diffraction angle of $2 \cdot 45° = 90°$, in particular wherein the reference light incident on the transmission diffraction grating arrangement encloses an angle of 45° with the diffraction plane and the diffracted reference light also encloses an angle of 45° with the diffraction plane. The diffracted reference light is then reflected by the first mirror, wherein the angle of the mirror plane a and/or the angle of the prism plane $\omega_2$ contribute to the reflected reference light being incident on the transmission diffraction grating arrangement at an angle other than 45° and therefore propagating to a large extent through the transmission diffraction grating arrangement without being diffracted.

This functionality can be achieved, as claimed according to the invention, in that the first mirror and/or the prism surface are arranged at an angle other than 45° in relation to the diffraction plane.

In this way, the system according to the invention can be used particularly advantageously in digital holography applications.

It is to be noted that the Littrow arrangement, i.e. a diffraction of 90°, is only possible for a central wavelength for an optical grating. Wavelengths deviating from this are diffracted by a different angular amount according to the angle dispersion.

The diffraction of 90° for the central wavelength can also vary slightly if the transmission diffraction grating arrangement is either not exactly at a 45° angle to the optical axis or the grating frequency does not quite meet the Littrow condition.

According to a further embodiment of the invention, the at least one first volume phase hologram grating of the transmission diffraction grating arrangement is configured so that it diffracts a first bandwidth $7\% \pm \Delta\lambda$ of wavelengths around a central wavelength 7, in a diffraction angle range around $90° \pm 40$ when operated in a Littrow arrangement.

The optical axis of the first diffraction element can point, coming from the first or second entrance surface, towards the diffraction plane and intersect the diffraction plane at a 45° angle. Unless explicitly required otherwise, it is assumed that in the state of the system according to the invention, reference light and object light are each incident on the diffraction plane along the optical axis.

According to the invention, each surface, i.e. the first and second entrance surface, the exit surface, and the prism surface, can be assigned a plane which extends along the respective surface. When reference is made to an angle between two surfaces, this also means the angle between the planes. Unless explicitly stated otherwise, the angle specifications refer to the internal angles of the prism arrangement.

In particular, the first entrance surface is limited by an edge with the exit surface on the one hand and by an imaginary intersection line of the diffraction plane with the first entrance plane on the other hand.

In particular, the exit surface is delimited by an edge with the first entrance surface on the one hand and by the imaginary intersection line of the diffraction plane with the exit plane and/or by the edge with the second entrance surface on the other hand.

Furthermore, direction specifications, orientations, and positions in the context of the invention are to be understood in particular for an optically unfolded state of the system. It is clear to a person skilled in the art that, for example, the direction of an optical axis can be changed by a deflecting mirror in the system, wherein in the optical-functional sense, no change in direction takes place, but only in the geometric sense. This understanding also has to be used to interpret the claims.

According to one embodiment of the invention, the diffraction plane of the first diffraction element encloses an angle $\omega_1$ with the first entrance surface of the first diffraction element, in particular wherein the angle is $30° \leq \omega_1 \leq 60°$, in particular wherein $\omega_1 = 45°$.

According to one embodiment of the invention, the diffraction plane of the first diffraction element encloses an angle $\omega_2$ with the prism surface of the first diffraction element, in particular wherein the angle is $30° \leq \omega_2 \leq 60°$, in particular wherein $\omega_2 = 45°$ or $\omega_2 = 45° \pm B$, in particular wherein $\omega_2$ is selected such that the prism surface extends parallel to the mirror plane of the first mirror.

According to one embodiment of the invention, the diffraction plane of the first diffraction element encloses an angle $\omega_3$ with the second entrance surface of the first diffraction element, in particular wherein the angle is $30° \leq \omega_3 \leq 60°$, in particular wherein $\omega_3 = 45°$.

According to one embodiment of the invention, the diffraction plane of the first diffraction element encloses an angle $\omega_4$ with the exit surface of the first diffraction element, in particular wherein the angle is $30° \leq \omega_4 \leq 60°$, in particular wherein $\omega_4 = 45°$ or $\omega_4 = 45° \pm B$, in particular wherein $\omega_4$ is selected such that the exit plane extends parallel to the mirror plane of the first mirror.

According to one embodiment of the invention, the first and second entrance surfaces of the first diffraction element are aligned parallel to one another.

According to a further embodiment of the invention, the angles $\omega_1$ and $\omega_3$ are equal to 45°. In this configuration, it is particularly possible to radiate reference light and object light perpendicularly onto the first and second entrance surfaces, since the entrance surfaces are perpendicular to the optical axis of the diffraction element.

According to one embodiment of the invention, the prism surface and the exit surface of the first diffraction element are aligned parallel to one another.

According to a further embodiment of the invention, the system comprises a first optical array detector, such as a camera, wherein the first array detector is configured to detect light exiting from the exit surface of the first diffraction element.

In particular, the first array detector is arranged on the side of the exit surface of the first diffraction element of the first holography arrangement.

Furthermore, it can be provided that the first array detector is arranged on the exit surface of the first diffraction element of the first holography arrangement and in particular wherein the first array detector is connected to the exit surface of the first diffraction element, so that there is at least no air gap between the exit surface and the array detector.

Alternatively, the first array detector can be spaced apart from the exit surface and can comprise an air gap between the exit surface and the array detector.

Furthermore, the first array detector can be configured to convert the detected light into an electrical signal that can be evaluated by an evaluation device of the system at least with regard to a two-dimensional intensity distribution of the detected light on the first array detector.

The array detector can provide a detection plane that extends along the array of the array detector, for example along a pixel matrix of the camera.

According to a further embodiment of the invention, it is provided that the detection plane of the first array detector encloses an angle of $\varepsilon=45°\pm\eta$ with $\eta>0°$ with the diffraction plane, in particular wherein $\eta=\beta$, in particular wherein the detection plane extends parallel to the first mirror. Furthermore, the exit plane can run parallel or co-planar to the detection plane.

In particular, $0°<\eta<20°$.

According to one embodiment of the invention, it can be provided that the detection plane encloses such an angle with the diffraction plane that light reflected from the detection plane is incident on the diffraction plane under a Littrow geometry, so that the reflected light is diffracted completely or at least largely by the transmission diffraction grating arrangement in the direction of the second entrance surface and can emerge there. This avoids a "ghosting" signal on the array detector caused by light reflected multiple times.

The above-mentioned embodiment of the invention has the advantage that it can prevent light reflected back from the array detector from reaching the first mirror again and from there being reflected back onto the array detector, where it generates an unwanted signal. By selecting the angle $\eta$, the light reflected from the array detector can be completely or largely diffracted by the first transmission diffraction grating arrangement in the direction of the second entrance surface.

According to a further embodiment of the invention, it is provided that the base surface of the first prism arrangement forms a parallelogram, in particular wherein the diffraction plane of the first diffraction element extends along a diagonal which extends in the base surface between the first entrance surface and the exit surface of the first diffraction element, in particular wherein i) the first entrance surface encloses an angle $\omega_1=45°\pm\rho_1$ with the diffraction plane of the first diffraction element and the prism surface encloses an angle $\omega_2=45°$ with the diffraction plane of the first diffraction element, wherein $\rho_1>0°$, in particular wherein $\rho_1>0.2°$, or ii) the first entrance surface encloses an angle $\omega_1=45°$ with the diffraction plane of the first diffraction element and the prism surface encloses an angle $\omega_2=45°\pm\rho_2$ with the diffraction plane of the first diffraction element, wherein $\rho_2>0°$, in particular wherein $\rho_2>0.2°$, or iii) the first entrance surface encloses an angle $\omega_1=45°\pm\rho_1$ with the diffraction plane of the first diffraction element and the prism surface encloses an angle $\omega_2=45°\pm\rho_2$ with the diffraction plane of the first diffraction element, wherein $\rho_1>0°$ and $\rho_2>0°$, in particular wherein $\rho_1>0.2°$ and $\rho_2>0.2°$, or iv) the first entrance surface encloses an angle $\omega_1=45°$ with the diffraction plane of the first diffraction element and the prism surface encloses an angle $\omega_2=45°$ with the diffraction plane of the first diffraction element, the base surface is a special parallelogram, namely a rectangle, preferably a square, in particular wherein the diffraction plane of the first diffraction element extends along a diagonal which extends in the base surface between the first entrance surface and the exit surface of the first diffraction element.

Each of the embodiments i) to iii) advantageously reduces potential interference reflections that arise when reference and/or object light enters or exits the prism arrangement.

In particular, embodiments ii) and iii) allow the first mirror to be arranged directly on the prism surface if, for example, the angle $\rho_2=\beta$ is selected.

Furthermore, in embodiments ii) and iii), the first array detector can also be arranged directly on the exit surface, as already mentioned above.

The advantages of a low-reflection geometry and the advantages previously mentioned for the array detector with regard to back reflection from the array detector in Littrow configuration are particularly evident, since the angle between the detection plane and the diffraction plane encloses $\varepsilon=45°\pm\eta$ with $\eta=\beta=\rho_2$, so that the detection plane extends parallel to the first mirror. Furthermore, the exit plane is essentially co-planar to the detection plane.

In particular, if at least the second entrance surface is anti-reflective, the proportion of the reference light reflected back again at the second entrance surface (which was reflected by the first array detector and diffracted via the transmission diffraction grating arrangement) can be neglected. Depending on the beam configuration, there may also be an inclination angle at the exit surface (for example embodiment iii), so that additional back reflection suppression is achieved.

The embodiments i) and iii) advantageously allow a polarization selection to be carried out simultaneously using the Brewster angle and, if necessary, polarization-rotating elements, such as a $\lambda/2$ plate, and/or to achieve a reduction in reflections. Reference light and object light are then to be coupled into the first diffraction element at an angle (i.e. not equal to) 90° so that the reference light and the object light around the central wavelength are incident on the transmission diffraction grating arrangement at an angle of 45°, i.e. in Littrow configuration.

According to embodiment iv), the base surface of the first prism arrangement is rectangular, in particular square.

Embodiment iv) provides a first diffraction element that is easy to produce. In this configuration, both the reference light and the object light can be irradiated perpendicular to the respective entrance surface and thus are incident on the transmission diffraction grating arrangement in the Littrow configuration. Furthermore, the angle $\alpha$ of the first mirror and, if necessary, the angle of the array detector are easily adjustable.

According to a further embodiment of the invention, the first mirror is arranged on the prism surface of the first holography arrangement.

This embodiment of the invention comprises the possibility that the first mirror is formed as a reflective layer on the prism surface. The reflective layer can be created on the prism surface by known methods.

This embodiment is a particularly robust and compact embodiment of the invention, since the first mirror is directly connected to the diffraction element and thus no assembly or adjustment of the mirror is necessary. Implicitly, the prism surface then encloses the angle α with the diffraction plane.

According to a further embodiment of the invention, the angle β is adjustable or adjusted via the first mirror.

According to a further embodiment of the invention, the first mirror is tiltable around at least one axis, so that the angle β is adjustable or adjusted via the first mirror.

In connection with this embodiment, the first mirror is in particular designed as a separate element which is optionally designed such that the angle β is adjustable.

According to a further embodiment of the invention, the optical transmission diffraction grating arrangement comprises a second volume phase hologram grating, which in particular also extends along or on the diffraction plane, wherein the first and the second volume phase hologram gratings have a maximum diffraction intensity, in particular for the first order of diffraction, at different central wavelengths, in particular wherein central wavelengths have a distance of at least the bandwidth of the first and the second volume phase hologram grating. In particular, this ensures that an undisturbed spectral separation of the two central wavelengths at the exit surface is guaranteed.

In comparison to a single volume phase hologram grating, this embodiment allows an enlarged spectral range to be made usable for the system, i.e. multiple different wavelengths, in particular spectral lines, can be spectrally separated at the exit surface via the first diffraction element without the first diffraction element requiring more installation space. For example, the central wavelength of the first volume phase hologram grating and five spectral lines from the bandwidth of the volume phase hologram grating could be diffracted via the first volume phase hologram grating, and, in addition to the central wavelength of the second volume phase hologram grating, a further five spectral lines within the bandwidth of the second volume phase hologram grating could be diffracted via the second volume phase hologram grating.

According to one embodiment of the invention, the first volume phase hologram grating has, for example, a central wavelength of 600 nm and a bandwidth of 10 nm.

According to one embodiment of the invention, the second volume phase hologram grating has, for example, a central wavelength of 620 nm and a bandwidth of 10 nm.

According to these two embodiments, the wavelength ranges of the first and second volume phase hologram gratings do not overlap because the central wavelengths are separated from one another by 20 nm, which corresponds to the sum of the bandwidths of the first and second volume phase hologram gratings. The greater the distance between the central wavelengths within the bandwidths, the fewer interactions are to be expected.

According to a further embodiment of the invention, the transmission diffraction grating arrangement comprises more than two volume phase hologram gratings, in particular wherein the volume phase hologram gratings have different central wavelengths. The central wavelengths can be spectrally spaced apart according to the bandwidth or more according to the principle outlined above.

According to one embodiment of the invention, the optical system has a second holography arrangement which comprises a second diffraction element which is formed by a second prism arrangement with at least a quadrangular base surface, in particular wherein the first and the second holography arrangement are arranged adjacent to one another along an optical axis of the first diffraction element, wherein a lateral surface of the second prism arrangement has the following lateral surface regions:

f) a first, in particular planar, entrance surface for reference light, which extends along a first entrance plane, wherein the first entrance surface can be part of a first end face, and g) a second, in particular planar, entrance surface for object light, which extends along a second entrance plane, wherein the first and the second entrance surface form opposite lateral surface regions of the second prism arrangement, wherein the second entrance surface can be part of a second end face, h) an exit surface, which extends along an exit plane and through which diffracted reference light and diffracted object light can exit from the second diffraction element, i) a prism surface opposite to the exit surface, wherein an optical transmission diffraction grating arrangement is arranged in the second diffraction element, which extends along a diffraction plane, which intersects the first entrance plane and the exit plane, between the first entrance surface and in particular the exit surface of the second diffraction element, in particular so that the transmission diffraction grating arrangement forms a triangular prism with the first entrance surface and the exit surface of the second diffraction element, in particular wherein the diffraction plane forms an imaginary lateral surface region of the triangular prism, wherein that the transmission diffraction grating arrangement of the second diffraction element comprises at least one first volume phase hologram grating, and that the second holography arrangement has a second, in particular planar, mirror having a second mirror plane on the side of the prism surface, wherein the second mirror plane encloses an angle α' with the diffraction plane, and the prism surface encloses an angle $\omega'_2$ with the diffraction plane, wherein at least one or both angles α', $\omega'_2$ is/are not equal to 45°, in particular wherein the angle α'=45°±β' with β'>0°, in particular wherein the angle $\omega'_2$=45°±ρ'$_2$ with ρ'$_2$>0°, in particular in order to achieve a maximum possible efficiency for object and reference light in the second holography arrangement.

Preferably, β' and/or ρ'$_2$ are greater than 0.2°.

Preferably, β' and/or ρ'$_2$ are less than 20°.

According to this embodiment of the invention, the angles β' and ρ'$_2$ are in particular selected such that reference light incident on the transmission diffraction grating arrangement at an angle of 45° is diffracted by the transmission diffraction grating arrangement in the direction of the prism surface of the second diffraction element and is reflected by the second mirror in such a way that the reflected reference light, due to an angle of incidence of the reflected reference light on the transmission diffraction grating arrangement of the second diffraction element, is diffracted again in the direction of the first entrance surface of the second diffraction element to a lesser extent, in particular a proportion that is less by at least 30%, than the reference light originally incident on the transmission diffraction grating arrangement from the side of the first entrance surface of the second diffraction element, and a remaining proportion of the reflected reference light propagates through the transmission diffraction grating arrangement in the direction of the exit surface of the second diffraction element.

In the state according to the invention, it is provided in particular that reference light enters the diffraction element via the first entrance surface of the second diffraction element, in particular in a collimated manner. There it is diffracted by the transmission diffraction grid arrangement in the direction of the prism surface of the second diffraction element. The second mirror reflects the diffracted reference light back in the direction of the transmission diffraction grating arrangement—but at an angle that can be calculated from Snell's law; in this way, at least part of the reflected reference light is not diffracted by the transmission diffraction grating arrangement, but is transmitted and propagated in the direction of the exit surface of the second diffraction element. According to the invention, the object light enters the second diffraction element via the second entrance surface and is diffracted by the transmission diffraction grating arrangement directly in the direction of the exit surface, where it is superimposed and in particular interferes with the reference light on a second array detector.

In the state of the system according to the invention, it is provided in particular that reference light is first radiated into the first holography arrangement and object light is first radiated into the second holography arrangement.

According to this embodiment, a second holography arrangement is disclosed which has substantially the same features as the first holography arrangement, in particular wherein the central wavelengths of the transmission diffraction grating arrangement of the first and second holography arrangements are different.

According to a further embodiment of the invention, the first volume phase hologram grating of the second holography arrangement has a central wavelength that is different from the first and/or the second volume phase hologram grating of the first holography arrangement.

In particular, the first and the second holography arrangement are arranged in relation to one another in such a way that the exit surfaces are aligned parallel and in particular co-planar—i.e. lying in the same plane—to one another, so that it is possible, for example, to use a single array detector to record the interference patterns on the exit surfaces of both diffraction elements.

According to an alternative embodiment of the invention, the first and the second holography arrangement are arranged relative to one another such that the exit surfaces of the first and the second diffraction element are aligned parallel to one another, wherein the exit surface of the first diffraction element is arranged on the side of the prism surface of the second diffraction element and the exit surface of the second diffraction element is arranged on the side of the prism surface of the first diffraction element. In particular, the first holography arrangement is rotated by 180° relative to the second holography arrangement, in particular around the optical axis. In particular, the diffraction planes of the first and second diffraction elements enclose an angle of typically 90°.

This offers the advantage that two independent array detectors can be used and there are fewer installation space problems regarding the array detectors.

According to a further embodiment of the invention, the first and the second holography arrangement are arranged relative to one another such that the first entrance surface of the second diffraction element of the second holography arrangement is arranged opposite and in particular parallel to the second entrance surface of the first diffraction element of the first holography arrangement, in particular wherein the diffraction planes of the first and the second diffraction elements are optically aligned parallel to one another.

It should be pointed out again here that the expressions 'opposite' and 'parallel' are to be understood in an optically functional sense and not necessarily in a strictly geometric sense.

According to one embodiment of the invention, the second diffraction element comprises an optical axis extending between the first and the second exit surface and intersecting the diffraction plane of the second diffraction element at an angle of 45°.

In particular, the first and second holography arrangements are arranged and aligned along a common optical axis that corresponds to the optical axis of the first diffractive element.

It is noted that all features, advantages, and embodiments relating to the first holography arrangement, the first diffraction element, the first mirror, or other components and disclosed in connection therewith are analogously applicable to the possible embodiments of the second holography arrangement and can be used for greater detail from the preceding paragraphs accordingly to specify the second holography arrangement.

The second mirror comprises a second mirror plane extending along a reflective layer of the second mirror, in particular wherein the second mirror consists of the reflective layer.

In the following, an angle of the second mirror with respect to a surface or a plane always means the angle of the second mirror plane of the second mirror with the surface or the corresponding plane.

According to the invention, each surface, i.e. the first and second entrance surface, the exit surface, and the prism surface of the second diffraction element, can be assigned a plane which extends along the respective surface. When reference is made to an angle between two surfaces, this also means the angle between the planes. Unless explicitly stated otherwise, the angle specifications refer to the internal angles of the second prism arrangement.

According to one embodiment of the invention, the diffraction plane of the second diffraction element encloses an angle $\omega'_1$ with the first entrance surface of the second diffraction element, in particular wherein the angle is $30° \leq \omega'_1 \leq 60°$, in particular wherein $\omega'_1 = 45°$.

According to one embodiment of the invention, the diffraction plane of the second diffraction element encloses an angle $\omega'_2$ with the prism surface of the second diffraction element, in particular wherein the angle is $30° \leq \omega'_2 \leq 60°$, in particular wherein $\omega'_2 = 45°$ or $\omega'_2 = 45° \pm \beta'$, in particular wherein $\omega'_2$ is selected such that the prism surface extends parallel to the mirror plane of the second mirror.

According to one embodiment of the invention, the diffraction plane of the second diffraction element encloses an angle $\omega'_3$ with the second entrance surface of the second diffraction element, in particular wherein the angle is $30° \leq \omega'_3 \leq 60°$, in particular wherein $\omega'_3 = 45°$.

According to one embodiment of the invention, the diffraction plane of the second diffraction element encloses an angle $\omega'_4$ with the exit surface of the second diffraction element, in particular wherein the angle is $30° \leq \omega'_4 \leq 60°$, in particular wherein $\omega'_4 = 45°$ or $\omega'_4 = 45° \pm \beta'$, in particular wherein $\omega'_4$ is selected such that the exit plane extends parallel to the mirror plane of the second mirror.

According to one embodiment of the invention, the first and second entrance surfaces of the second diffraction element are aligned parallel to one another.

According to one embodiment of the invention, the prism surface and the exit surface of the second diffraction element are aligned parallel to one another.

According to a further embodiment of the invention, the angles ω' and w's are equal to 45°. In this configuration, it is particularly possible to radiate reference light and object light perpendicularly onto the first and second entrance surfaces, since the entrance surfaces are perpendicular to the optical axis of the second diffraction element.

According to one embodiment of the invention, the first entrance surface of the first diffraction element and the second entrance surface of the second diffraction element are aligned parallel to one another.

According to one embodiment of the invention, the angles β' and β are of different sizes.

The different angles β' and β can advantageously be adapted according to the central wavelengths and bandwidths of the volume phase hologram gratings in the first and second diffraction elements.

According to an alternative embodiment of the invention, the angles β' and β are identical.

According to a further embodiment of the invention, the angles $ω'_1$ and $ω_1$ are identical.

According to a further embodiment of the invention, the angles $ω'_2$ and we are identical.

According to a further embodiment of the invention, the angles $ω'_3$ and $ω_3$ are identical.

According to a further embodiment of the invention, the angles $ω'_4$ and $ω_4$ are identical.

According to a further embodiment of the invention, the first and the second diffraction element have the same geometry and in particular size, i.e. are identical except for the optical characteristics of the transmission diffraction grating arrangement.

The first and/or second entrance surface of the first and/or second diffraction element can be provided with an anti-reflection coating. Likewise, the exit surface and/or the prism surface of the first and/or the second diffraction element can be provided with an anti-reflection coating.

In the state according to the invention, it is provided in particular that reference light enters the first diffraction element via the first entrance surface of the first diffraction element, in particular in a collimated manner. There it is partially diffracted by the transmission diffraction grid arrangement in the direction of the prism surface of the first diffraction element. A further part of the reference light, which due to its wavelength is not diffracted at the transmission diffraction grating arrangement of the first diffraction element, propagates in the direction of the second diffraction element and is diffracted there by the transmission diffraction grating arrangement of the second diffraction element in the direction of the prism surface of the second diffraction element.

The same applies in particular to the object light, which first enters via the second entrance surface of the second diffraction element and then partially propagates further in the direction of the first diffraction element. At the exit surfaces or the array detectors of the first and second diffraction elements, the reference light is then accordingly superimposed with the object light in a spectrally resolved manner.

According to a further embodiment of the invention, the system comprises a second optical array detector, such as a camera, wherein the second array detector is configured to detect light exiting from the exit surface of the second diffraction element.

In particular, the second array detector is arranged on the side of the exit surface of the second diffraction element of the second holography arrangement.

Furthermore, it can be provided that the second array detector is arranged on the exit surface of the second diffraction element of the second holography arrangement while avoiding the formation of an air gap, thus directly, and in particular wherein the second array detector is connected to the exit surface of the second diffraction element, so that there is at least no air gap between the exit surface and the array detector.

Furthermore, the second array detector can be configured to convert the detected light into an electrical signal that can be evaluated by the evaluation device, such as a computer, of the system at least with regard to a two-dimensional intensity distribution of the detected light on the second array detector.

The second array detector can provide a detection plane that extends along the array of the second array detector, for example along a pixel matrix of the camera.

According to a further embodiment of the invention, it is provided that the detection plane of the second array detector encloses an angle of $ε'=45°±η'$ with $η'>0°$ with the diffraction plane, in particular wherein $η'=β'$, in particular wherein the detection plane extends parallel to the second mirror. Furthermore, the exit plane can run parallel or co-planar to the detection plane.

In particular, $0°<η'<20°$.

According to one embodiment of the invention, it can be provided that the detection plane encloses such an angle with the diffraction plane the second diffraction element that light reflected from the detection plane is incident on the diffraction plane under a Littrow geometry, so that the reflected light is diffracted completely or at least largely by the transmission diffraction grating arrangement the second holography arrangement in the direction of the second entrance surface the second diffraction element and can exit there. This avoids a "ghosting" signal on the second array detector caused by light reflected multiple times.

The above-mentioned embodiment of the invention has the advantage that it can prevent light reflected back from the second array detector from reaching the second mirror again and from there being reflected back onto the second array detector, where it generates an unwanted signal. By selecting the angle $η'$, the light reflected from the second array detector can be completely or largely diffracted by the first transmission diffraction grating arrangement in the direction of the second entrance surface of the second diffraction element.

According to a further embodiment of the invention, it is provided that the base surface of the second prism arrangement forms a parallelogram, in particular wherein the diffraction plane of the second diffraction element extends along a diagonal which extends in the base surface between the first entrance surface and the exit surface of the second diffraction element, in particular wherein i) the second entrance surface encloses an angle $ω'_1=45°±ρ'_1$ with the diffraction plane of the second diffraction element and the prism surface encloses an angle $ω'_2=45°$ with the diffraction plane of the second diffraction element, wherein $ρ'_1>0°$, in particular wherein $ρ'_1>0.2°$, or ii) the first entrance surface encloses an angle $ω'_1=45°$ with the diffraction plane of the second diffraction element and the prism surface encloses an angle $\omega'_2=45°\pm\rho'_2$ with the diffraction plane of the second diffraction element, wherein $\rho'_2>0°$, in particular wherein $\rho'_1>0.2°$, or iii) the first entrance surface encloses an angle $\omega'_1=45°\pm\rho'_1$ with the diffraction plane of the second diffraction element and the prism surface encloses an angle $\omega'_2=45°\pm\rho'_2$ with the diffraction plane of the second diffraction element, wherein $\rho'_1>0°$ and $\rho'_2>0°$, in particular wherein $\rho'_1>0.2°$ and $\rho'_2>0.2°$, or iv) the first entrance surface encloses an angle $\omega'_1=45°$ with the diffraction plane of the second diffraction element and the prism surface encloses an angle $\omega'_2=45°$ with the diffraction plane of the second diffraction element, the base surface is a special parallelogram, namely a rectangle, preferably a square, in particular wherein the diffraction plane of the first diffraction element extends along a diagonal which extends in the base surface between the first entrance surface and the exit surface of the first diffraction element.

Each of the embodiments i) to iii) advantageously reduces potential interference reflections that arise when reference and/or object light enters or exits the second prism arrangement.

In particular, embodiments ii) and iii) allow the second mirror to be arranged directly on the prism surface of the second diffraction element if, for example, the angle $\rho'_2=\beta'$ is chosen.

Furthermore, in embodiments ii) and iii), the second array detector can also be arranged directly on the exit surface, as already mentioned above.

The advantages of a low-reflection geometry and the advantages previously mentioned for the array detector with regard to back reflection from the array detector in Littrow configuration are particularly evident, since the angle between the detection plane and the diffraction plane is $\epsilon'=45°\pm\eta'$ with $\eta'=\beta'=\rho'_2$, so that the detection plane extends parallel to the second mirror. In addition, the exit plane is essentially co-planar to the detection plane.

In particular, if at least the second entrance surface is anti-reflective, the proportion of the reference light reflected back again at the second entrance surface (which was reflected by the second array detector and diffracted via the transmission diffraction grating arrangement) can be neglected. Depending on the beam configuration, there may also be an inclination angle at the exit surface (for example embodiment iii), so that additional back reflection suppression is achieved.

The embodiments i) and iii) advantageously allow a polarization selection to be carried out simultaneously using the Brewster angle and, if necessary, polarization-rotating elements, such as a $\lambda/2$ plate, and/or to achieve a reduction in reflections. Reference light and object light are then to be coupled into the first diffraction element at an angle (i.e. not equal to) 90° so that the reference light and the object light around the central wavelength are incident on the transmission diffraction grating arrangement at an angle of 45°, i.e. in Littrow configuration.

According to embodiment iv), the base surface of the second prism arrangement is rectangular, in particular square.

The embodiment iv) provides a second diffraction element that is easy to produce. In this configuration, both the reference light and the object light can be irradiated perpendicular to the respective entrance surface and thus are incident on the transmission diffraction grating arrangement in the Littrow configuration. Furthermore, the angle $\alpha'$ of the second mirror and, if necessary, the angle s' of the second array detector are easily adjustable.

According to a further embodiment of the invention, the second mirror is arranged on the prism surface of the second holography arrangement.

This embodiment of the invention comprises the possibility that the second mirror is formed as a reflective layer on the prism surface. The reflective layer can be created on the prism surface by known methods.

Furthermore this embodiment enables a particularly robust and compact embodiment of the invention, since the second mirror is directly connected to the second diffraction element and thus no assembly or adjustment of the mirror is necessary. Implicitly, the prism surface then encloses the angle $\omega'_2=\alpha'$ with the diffraction plane of the second diffraction element.

According to a further embodiment of the invention, the angle $\beta'$ is adjustable or adjusted via the second mirror.

According to a further embodiment of the invention, the second mirror is tiltable around at least one axis, so that the angle $\beta'$ is adjustable or adjusted via the second mirror.

In connection with this embodiment, the second mirror is in particular designed as a separate element which is optionally designed such that the angle $\beta'$ is adjustable.

According to a further embodiment of the invention, the optical transmission diffraction grating arrangement of the second diffraction element comprises a second volume phase hologram grating, which in particular also extends along or on the diffraction plane, wherein the first and the second volume phase hologram gratings of the second diffraction element have a maximum diffraction intensity, in particular for the first order of diffraction, at different central wavelengths, in particular wherein central wavelengths have a distance of at least the bandwidth of the first and the second volume phase hologram grating of the second diffraction element. In particular, this ensures that a spectral separation of the central wavelengths at the exit surface of the second diffraction element is guaranteed.

In comparison to a single volume phase hologram grating, this embodiment allows an enlarged spectral range to be made usable for the system, i.e. multiple different wavelengths, in particular spectral lines, can be spectrally separated at the exit surface via the second diffraction element without the second diffraction element requiring more installation space.

According to one embodiment of the invention, the first volume phase hologram grating has, for example, a central wavelength of 940 nm and a bandwidth of 10 nm.

According to one embodiment of the invention, the second volume phase hologram grating has, for example, a central wavelength of 960 nm and a bandwidth of 10 nm.

According to these two embodiments, the wavelength ranges of the first and second volume phase hologram gratings do not overlap because the central wavelengths are separated from one another by 20 nm, which corresponds to the sum of the bandwidths of the first and second volume phase hologram gratings of the second diffraction element. The greater the distance between the central wavelengths within the bandwidths, the fewer interactions are to be expected.

According to a further embodiment of the invention, the transmission diffraction grating arrangement of the second diffraction element comprises more than two volume phase hologram gratings, in particular wherein the volume phase hologram gratings have different central wavelengths. The central wavelengths can be spectrally spaced apart according to the bandwidth or more according to the principle outlined above.

In combination with the first holography arrangement, a second spectral range can be used for digital holography.

In particular, the transmission diffraction grating arrangements of the first and the second diffraction elements are configured for different central wavelengths, i.e. the central wavelengths of the transmission diffraction grating arrangements are also here spectrally spaced apart according to the principle set out above in accordance with the bandwidths or more.

According to a further embodiment of the invention, it is provided that the second entrance surface of the first diffraction element is connected to the first entrance surface of the second diffraction element, in particular adhesively bonded or welded, in particular wherein the first diffraction element is formed integrally with the first entrance surface of the second diffraction element along its second entrance surface.

The embodiment allows a compact, adjustment-free construction of the optical system, since at least the first and the second diffraction elements have a rigid alignment and position with respect to one another. If the first and second mirrors are also integrally formed with the diffraction element, the robustness is increased. Furthermore, both the first and the second array detector can be connected to the respective diffraction element.

Depending on the nature of the connection of the respective entrance surfaces, the connected entrance surfaces may have an essentially imaginary nature (for example because they are fused with one another). In particular, however, the invention itself is intended to comprise a monolithic embodiment of the first and second diffraction elements, at least within the scope of the interpretation and general understanding of a person skilled in the art.

According to a further embodiment of the invention, the optical system has a collimation optical unit for reference light on the side of the first entrance surface of the first holography arrangement, which has an optical axis which runs in the direction of the first entrance surface of the first holography arrangement, in particular wherein the optical axis runs laterally, i.e. can be offset, and wherein the collimation optical unit is designed to collimate laser light in the form of reference light before it enters through the first entrance surface of the first diffraction element. In particular, the collimation optical unit is aligned with its optical axis in such a way that reference light collimated thereby propagates along the optical axis of the first diffraction element after entering the first diffraction element, so that it is incident on the diffraction plane of the first diffraction element at a 45° angle. The lateral offset can be designed in such a way that the collimated light, after reflection at the reference mirror, is again incident on the exit surface or the detector array centrally with its angle β relative to the optical axis.

The term "collimated" is to be interpreted in particular in such a way that the reference light has only minimal wavefront curvature, at least for one wavelength. At different wavelengths, the convergence or divergence of the light beam or wave field increases depending on the wavelength. These chromatically related deviations from the ideal collimation are also comprised by the term "collimated" in the context of this invention. In addition, deviations due to adjustment and system tolerances are also to be understood under the term "collimated". In particular, the term "collimated" is also to be understood as a convergence and/or divergence of the light beam up to a divergence or convergence angle $\xi$ which lies in the range $0°<\xi\leq2*\beta$ or $2*\rho_2$ and/or $0°<\xi\leq2*\beta'$ or $2*\rho'_2$, within the scope of the invention.

According to a further embodiment of the invention, the optical system comprises an objective lens for object light, which has an optical axis which extends in the direction of the second entrance surface of the first and/or the second holography arrangement, wherein the objective lens is arranged in the optical system such that light propagating from the objective lens in the direction of the second entrance surface of the first and/or the second diffraction element is collimated when the light is emitted, in particular reflected or scattered, in and/or near a focal plane of the objective lens in the direction of the objective lens, in particular wherein the light is object light.

The term "near" in relation to a focal plane or a focus or focal point in the context of the specification is to be understood in particular as a tolerance indication, since deviations from the ideal optical arrangement of the components or deviations from an ideal beam/wave path of the light can be easily handled by the system according to the invention. In this context, the term "near" can be understood, for example, as a tolerance range with respect to a focal length of the objective lens, so that for a nominal focal length f, a deviation range of ±f/5 is defined by the term "near". An analogous understanding can also apply to the other components of the system.

According to the laws of imaging optics, the light that is closer or further away from the focal plane of the objective lens is divergent or convergent when it is incident on the second entrance surface. Depending on the degree of divergence/convergence, however, this light can also contribute to imaging in the digital holography method.

The objective lens is aligned with its optical axis in particular such that object light originating from a focal point of the objective lens propagates along the optical axis of the first or second diffraction element after entering the first or second diffraction element, so that it is incident on the diffraction plane of the first or second diffraction element at a 45° angle.

The objective lens can consist of one or more lenses or lens elements.

It is also to be noted that according to the invention, in particular only one objective lens is provided, even if two holography arrangements are included in the system. The objective lens is then located closer to the side of the second diffraction element and its second entrance surface.

According to a further embodiment of the invention, the system comprises the following components:

a laser light source which is configured to provide laser light having one or more central wavelengths, in particular wherein the laser light source comprises one or more lasers, in particular wherein each laser is configured to emit laser light comprising at least one central wavelength, wherein each laser emits at least one, preferably a plurality of laser lines in a wavelength range around the central wavelength of the laser, a first optical fiber, in particular a polarization-maintaining single-mode fiber, which is configured to guide the laser light of the laser light source to an input aperture of the collimation optical unit, so that the collimation optical unit can guide the collimated laser light in the form of reference light to the first holography arrangement, a second optical fiber, in particular a polarization-maintaining single-mode fiber, which is configured to guide the laser light from the laser light source to an output aperture of the optical system, from which an object to be detected is to be illuminated using laser light in the form of object light.

This embodiment allows the polarization of the reference and object light to be controlled. In particular, a volume phase hologram grating diffracts s-polarized light significantly better than p-polarized light, so that the system is particularly configured so that the reference light and object light are particularly s-polarized after they exit the first and second optical fibers.

According to a further embodiment of the invention, the system comprises a fiber splitter, in particular a polarization-maintaining fiber splitter, which is configured to split the laser light of the laser light source and to couple it into the at least one first and second optical fiber, in particular wherein the fiber splitter and the at least one first and second optical fiber are comprised in an integrated optical element.

According to one embodiment of the invention, the system has an imaging optical unit which is designed to project object light, in particular object light exiting from the second fiber, in the form of an intensity pattern, in particular onto an object to be detected, wherein the intensity pattern consists of at least one illuminated region but preferably a plurality of disjoint illuminated regions, in particular wherein the illuminated regions of the pattern are point-shaped or circular, in particular wherein the object light reflected by the object is detected by the objective lens.

This form of the intensity pattern allows parallel recording and evaluation of multiple object regions using a plurality of wavelengths.

Complete detection can be carried out by moving the pattern on the object so that the object is optically scanned and detected in regions.

In this way, a surface of an object can be scanned using the intensity pattern, wherein depth information and lateral location information can be generated for each region via the first and/or second holography arrangement, so that 3D information can be generated from the object surface scanned using the object light.

According to a further embodiment of the invention, the system has a housing, in particular a waterproof housing, wherein the housing comprises the first and/or the second holography arrangement, the first collimation optical unit, and the objective lens, in particular wherein the laser light source is arranged outside the housing and is connected to the housing via at least the flexible optical fiber line.

In particular, the laser light source can be arranged either in the housing or outside thereof and is configured to couple reference light originating from the laser light source and object light coherent therewith into the at least one first and second fiber via a fiber splitter, preferably in the housing.

Such an optical system having laser light source and fiber splitter can be integrated in a comparatively compact module, wherein at least one reference arm of the system, i.e. the part of the system through which the reference light is guided, and in particular the first and/or second holography arrangement, can be part of the integrated module. Such a system requires only minimal space within the housing, making it suitable for minimally invasive medical applications.

According to a further embodiment of the invention, the system is configured to provide the laser light which comprises wavelengths from at least two wavelength ranges, wherein a first wavelength range of the two wavelength ranges is arranged around a central wavelength and comprises wavelengths in particular in the form of spectral lines, for example in the form of laser lines, which lie outside a second wavelength range, wherein the second wavelength range is arranged around a different central wavelength which comprises two wavelength ranges and wavelengths in particular in the form of spectral lines, wherein in particular the first and the second wavelength range each comprise a spectral range of not more than 50 nm, in particular not more than 15 nm, in particular wherein the spectral lines of the wavelength ranges each have a line width of not more than 0.5 nm, in particular not more than 0.2 nm.

In particular, such a system then has two volume phase hologram gratings, each of which is configured for one of the two central wavelengths, i.e. is configured to diffract the central wavelength for which the volume phase hologram grating is configured and to leave the other central wavelength undiffracted.

The two volume phase hologram gratings can both be arranged in the first diffraction element or in the second diffraction element. Alternatively, each of the two diffraction elements can comprise one of these volume phase hologram gratings.

A further aspect of the invention relates to a human or veterinary medical endoscope system comprising the optical system according to the invention for creating digital holographic images.

The endoscope system can be configured to create holographic video recordings and display a 3D representation of the detected object on a display screen.

DESCRIPTION OF THE FIGURES

Further features and advantages of the invention are explained below with reference to the figure description of exemplary embodiments. Angles and lengths may be exaggerated or understated in the figures and serve only to illustrate the invention. In particular, it is advantageous if each of the entrance surfaces of the diffraction element is larger than its exit surface.

In the figures:

In FIG. 1, an exemplary general embodiment of the system 1 according to the invention is shown schematically as a 2D section.

Figure 1:
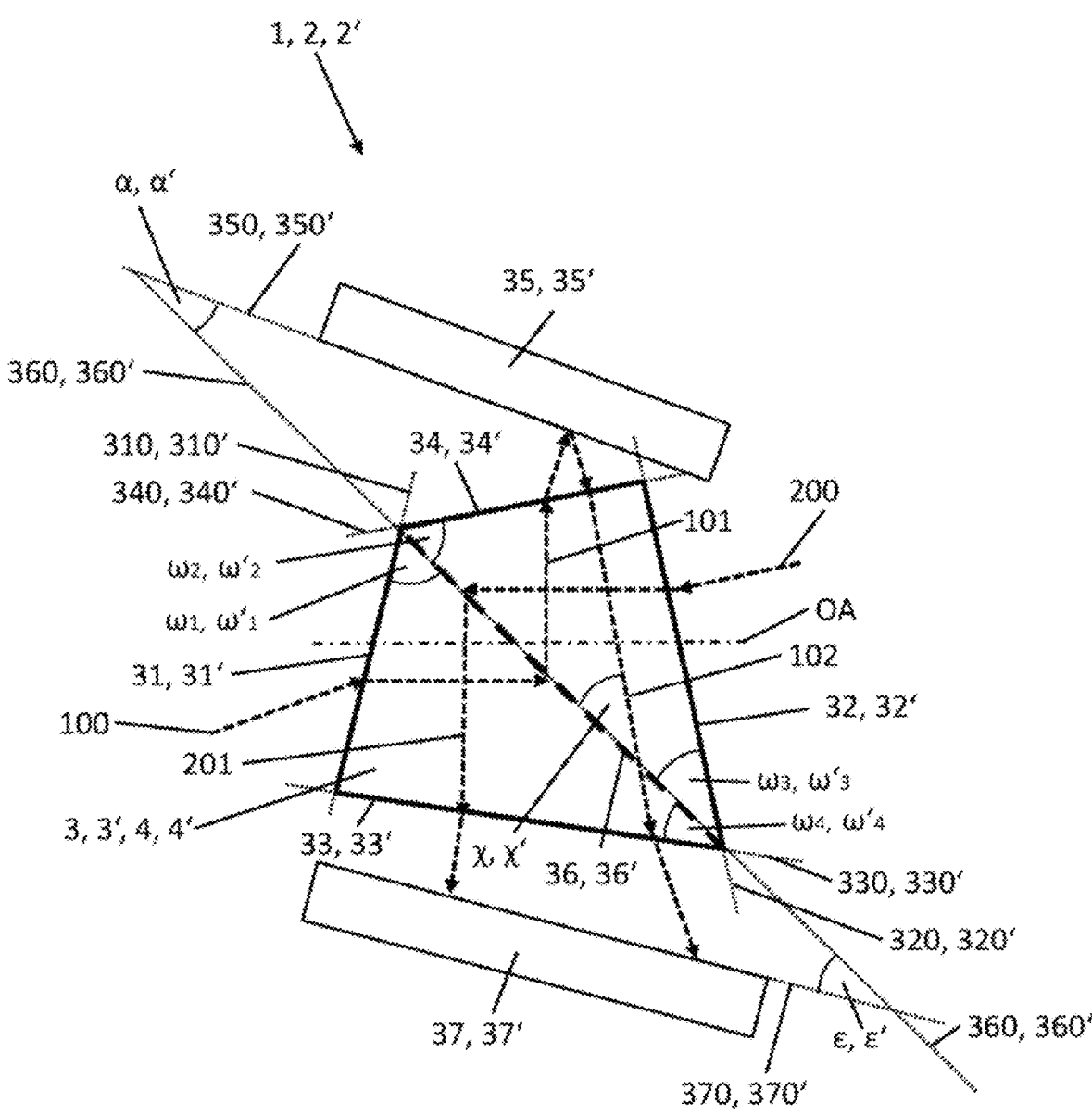
FIG. 1 shows a schematic sectional view of a first general embodiment of the holography arrangement of the system according to the invention.

The optical system 1 has a first holography arrangement 2 which comprises a first diffraction element 3, a first mirror 35, and a first array detector 37.

Figure 5:
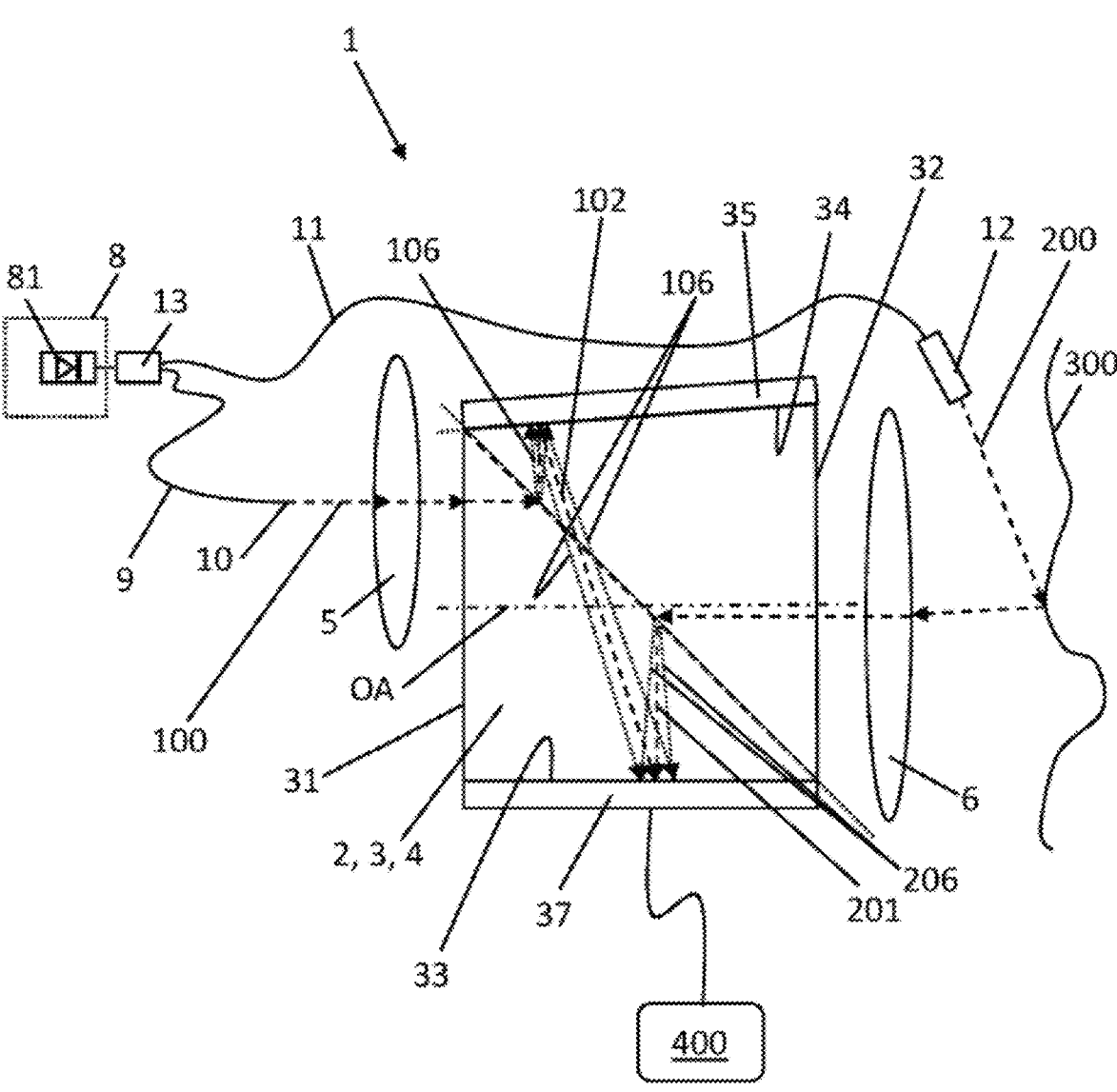
FIG. 5 shows a schematic sectional view of an embodiment of the system according to the invention having a holography arrangement.
Figure 6:
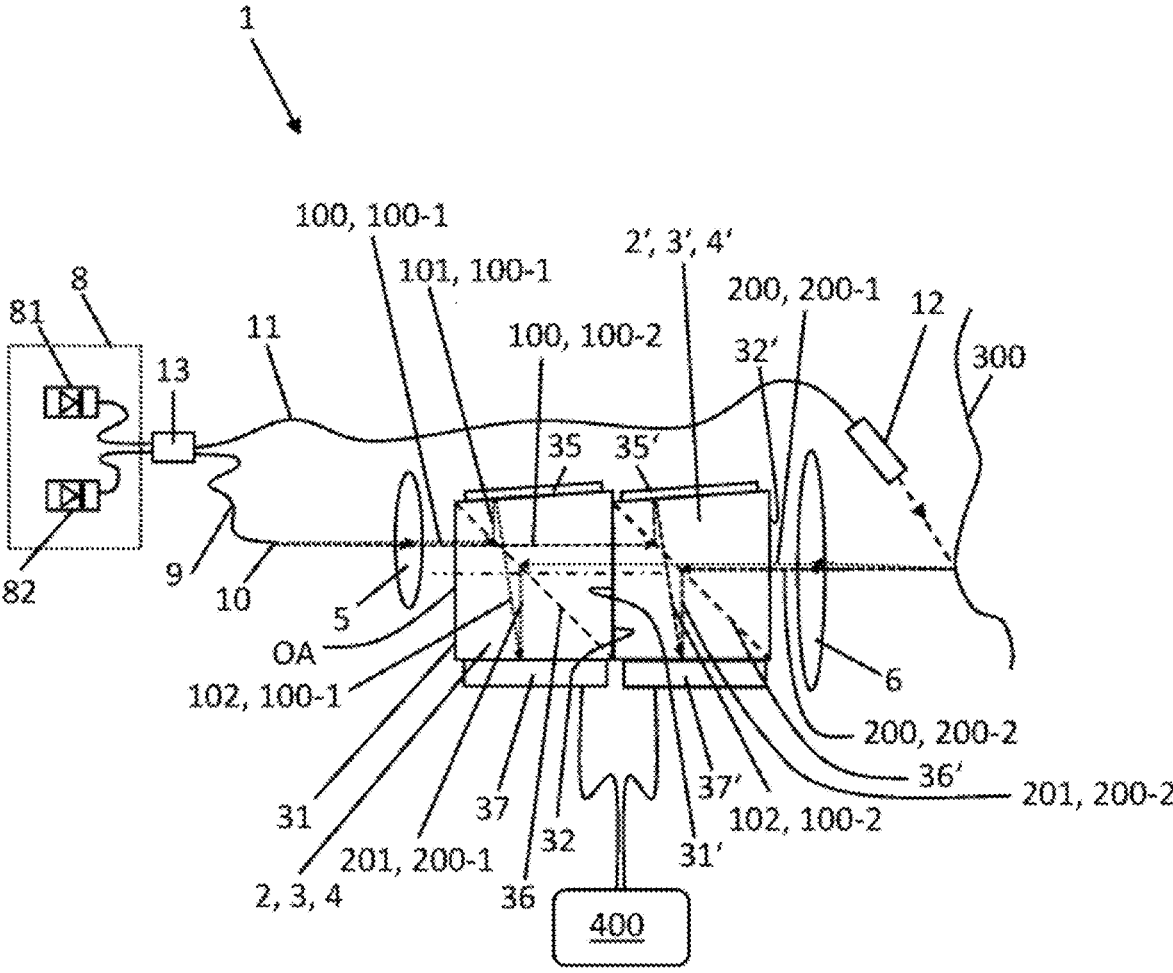
FIG. 6 shows a schematic sectional view of an embodiment of the system according to the invention having two holography arrangements.

The system 1 furthermore has a collimation optical unit 5 and an objective lens 6 (cf. FIGS. 5 and 6). A laser light source 8 of the system 1 is configured (cf. FIGS. 5 and 6) to provide reference light 100 and object light 200 for the system 1.

A variant of the system can comprise a second holography arrangement 2', which in turn comprises a second diffraction element 3', a second mirror 35, and a second array detector 37. Since essential features of the first and second holography arrangements 2, 2' are arranged in the same way and are functionally related in the same way, the corresponding reference numerals of the elements and components are also indicated for the second holography arrangement 2' in FIGS. 1 to 4. The reference numerals for the second holography arrangement 2' correspond to the reference numerals for the first holography arrangement 2 plus a "'". In the following text, the first holography arrangement 2 is first described, wherein the same or at least analogous applies to the second holography arrangement 2'.

The first holography arrangement 2 comprises a solid (e.g. glass or polymer) prism arrangement 4, which forms the first diffraction element 3, in this case having a quadrangular base surface, the edges of which are enclosed by the lateral surface of the prism arrangement 4. The lateral surface comprises four lateral surface regions, namely a first and a second entrance surface 31, 32, which can each be part of an end face of the first diffraction element 3, an exit surface 33, and a prism surface 34. Except for the prism surface 34, which can also be designed to be reflective, the first and second entrance surfaces 31, 32 and the exit surface 33 are transparent.

Each surface of the prism arrangement 4 can be assigned a corresponding plane (shown as dotted lines) that extends along the respective surface. Accordingly, the first entrance plane 310 extends along the first entrance surface 31, the second entrance plane 320 extends along the second entrance surface 32, the exit plane 330 extends along the exit surface 33, and the prism plane 340 extends along the prism surface 34.

The first prism arrangement 4 furthermore comprises a transmission diffraction grating arrangement 36 which extends along a diffraction plane 360 in the first diffraction element 3. The transmission diffraction grating arrangement 36 comprises at least a first volume phase hologram grating.

A first mirror plane 350 extends through the first mirror 35 along a reflective surface of the first mirror 35. The first mirror 35 is arranged on the side of the prism surface 34.

Between the first and the second entrance surface 31, 32, an optical axis OA of the first diffraction element 3 can be defined, which intersects the diffraction plane 360 at a 45° angle.

The first holography arrangement 2 is now configured such that the first mirror plane 350 encloses an angle $\alpha$ with the diffraction plane 360 of the first diffraction element 3, and wherein the prism plane 340 encloses an angle $\omega_2$ with the diffraction plane 360, wherein either both or only one of these angles $\alpha$, $\omega_2$ is selected such that reference light 101 diffracted by the transmission diffraction grating arrangement 36 in the direction of the prism surface 34 is reflected by the first mirror 35 such that the reflected reference light 102 is diffracted again in the direction of the first entrance surface 31 due to an angle of incidence of the reflected reference light 102 on the transmission diffraction grating arrangement 36, in particular by a smaller proportion, in particular less than 30%, than the reference light 100 originally incident on the transmission diffraction grating arrangement, and the remaining proportion the reflected reference light 102 is propagated through the transmission diffraction grating arrangement 36 in the direction of the exit surface 33.

This goal is achieved particularly well starting from a Littrow configuration, i.e. when reference light 100 irradiated into the diffraction element 3 and collimated propagates along the optical axis OA of the first diffraction element 3, when the angle $\alpha=45°\pm\beta$, with $\beta\neq0°$ and/or when the angle $\omega_2=45°\pm\rho_2$, with $\rho_2\approx0°$. In particular, the angle $\beta$ and/or the angle $\rho_2$ is to have an absolute value in the range 0.2° and 20°, in particular in the range 0.5° and 20°, so that a is in the range 25° to 44.5° or 45.5° to 65° and/or so that $\omega_2$ is in the range 25° to 44.5° or 45.5° to 65°.

To achieve the desired effect, it is sufficient if either the first mirror 35 or the prism surface 34 forms an angle $\alpha$ or $\omega_2$ not equal to 45°. However, as shown in FIG. 1, it is possible that both the first mirror 35 and the prism surface 34 enclose an angle other than 45° with the diffraction plane.

According to the invention, it is particularly provided that reference light 100 in the collimated state is incident on the transmission diffraction grating arrangement 36 at an angle of 45°. Collimation and propagation direction of the reference light in the diffraction element 3 can be achieved via the position and orientation of the collimation optical unit 5 (not shown in FIG. 1).

According to the invention, the reference light 100 can comprise at least one central wavelength 100-1 at which the transmission diffraction grating arrangement 36 diffracts the first order of diffraction by 90° relative to the optical axis OA of the diffraction element 3 in the Littrow configuration, so that the diffracted reference light 102 of this wavelength 100-1 propagates away from the transmission diffraction grating arrangement 36 by 45°. Depending on the angle $\omega_2$ of the prism surface 34 and the angle $\alpha$ of the first mirror 35, the diffracted reference light 102 of the central wavelength 100-1 reflected by the mirror 35 is no longer incident on the transmission diffraction grating arrangement at the 45° angle. If the angle $\chi$ at which the reflected reference light 102 is incident on the transmission diffraction grating arrangement 36 lies outside the bandwidth of the transmission diffraction grating arrangement 36, the reflected reference light 102 propagates undiffracted through the transmission diffraction grating arrangement 36 and is incident on the exit surface 33 of the first diffraction element 3 where it is detected by a first array detector 37, such as a camera.

On the other side of the diffraction element 3, i.e. on the side of the second entrance surface 32, laser light in the form of object light 200 is projected onto an object 300 to be detected (cf. FIG. 5 or 6) by means of an imaging optical unit 12 (cf. FIG. 5 or 6) of the system 1. The object light 200 is projected onto the object 300 in the form of an intensity pattern, wherein the intensity pattern (not shown) consists of a plurality of laterally offset and laterally non-overlapping spots, i.e. a plurality of illuminated areas that are separated from one another by non-illuminated areas.

Object light 200 from an illuminated area of the intensity pattern is reflected or scattered back by the object 300 in the direction of the holography arrangement 2. To collect the object light 200, the system 1 has an objective lens 6. In operation according to the invention, the objective lens 6 is held at a distance from the intensity pattern which approximately corresponds to the focal length of the objective lens 6. In this way, the object light 200 of the intensity pattern is collimated. Perfect collimation presumes the object region in the focus of the objective lens 6. Regions outside the focal plane, i.e. at a different z-distance, would generate a slightly curved wave field. The mathematical consideration of such a wave field is known to a person skilled in the art Therefore, the image via the radiation vectors is mainly used.

The collimated object light 200 is incident on the second entrance surface 32 of the first diffraction element 3 (or if the system has two diffraction elements 3, 3', the second entrance surface 32' of the second diffraction element 3', see, for example, FIG. 6) in such a way that it is incident on the transmission diffraction grating arrangement 36, 36' in the diffraction element 3, 3' at approximately an angle of 45°, i.e. in Littrow configuration. For this purpose, the objective lens 6 can have a specific position and orientation relative to the optical axis OA of the diffraction element 3, 3' depending on the configuration of the diffraction element 3, 3'—for example, if the second entrance surface 32, 32' of the diffraction element 3, 3' forms an angle other than 90° with the optical axis OA of the diffraction element 3, 3', the optical axis of the objective lens 6 is possibly to be arranged at an angle to the optical axis OA of the diffraction element 3, 3', so that the collimated object light 200 propagates along the optical axis OA of the diffraction element 3, 3' after entering the diffraction element 3, 3', so that the Littrow configuration is ensured. The transmission diffraction grating arrangement 36 then diffracts the object light 201 towards the exit surface 33 where it is superimposed with the diffracted and reflected reference light 102 and possibly forms an interference pattern that is detected by the first array detector 37. From the interference patterns, the 3D information of the object 300 can be calculated in a known manner.

The first array detector 37 can be arranged along its detection plane 370 at an angle $\varepsilon=45°\pm\eta$ not equal to 45° in relation to the diffraction plane 360. This can advantageously suppress reflections.

In the general variant of the holography arrangement 2, 2' (as shown, for example, in FIG. 1), the lateral surface areas of the first diffraction element 3 can enclose angles other than 45° in relation to the diffraction plane 360. This can also have beneficial effects regarding interfering reflections from surfaces. In particular, the following angles are shown in FIG. 1:

Angle $\omega_1$, which is enclosed by the first entrance surface and the diffraction plane, wherein $\omega_1$ can be in the range of 30° to 60°.

Angle $\omega_2$, which is enclosed by the prism surface and the diffraction plane. An optional angular deviation from 45° of the angle $\omega_2$ is described by the angle $\rho_2$.

Angle $\omega_3$, which is enclosed by the second entrance surface and the diffraction plane, wherein $\omega_3$ can be in the range of 30° to 60°.

Angle $\omega_4$, which is enclosed by the exit surface and the diffraction plane, wherein $\omega_4$ can be in the range of 30° to 60°.

Angle $\alpha$, which is enclosed by the first mirror and the diffraction plane. An optional angular deviation from 45° of the angle $\alpha$ is described by the angle $\beta$.

Angle $\varepsilon$, which is enclosed by the first array detector, more precisely with the detection plane of the array detector and the diffraction plane. An optional angular deviation from 45° is described here by the angle $\eta$.

As already mentioned at the beginning, the angle designations, the indicated angle relationships between the surfaces and planes of the first holography arrangement 2, as well as the mode of operation (for example, Littrow arrangement) of the first holography arrangement 2 can be transferred to a second holography arrangement 2' in an analogous manner. This means, for example, that instead of the first diffraction element 3, a second diffraction element 3' is present, instead of the first mirror 35, a second mirror 35' is part of the second holography arrangement 2', and instead of a first array detector 37, a second array detector 37' is arranged on the side of the exit surface 33' of the second diffraction element 3'. For this reason, the corresponding angle designations and reference signs for the components of the second holography arrangement 2' are also shown accordingly in FIG. 1, for which essentially the same applies as for the first holography arrangement 2 with regard to the angle and mode of operation. In detail, this means:

Angle $\omega'_1$ is enclosed by the first entrance surface 31' or entrance plane 310' and the diffraction plane 360' of the second diffraction element 3', wherein $\omega'_1$ can be in the range of 30° to 60°.

Angle $\omega'_2$ is enclosed by the prism surface 34' and the diffraction plane 360' of the second diffraction element 3'. An optional angular deviation from 45° of the angle $\omega'_2$ is described by the angle $\rho'_2$.

Angle $\omega'_3$ is enclosed by the second entrance surface 32' and the diffraction plane 360' of the second diffraction element 3', wherein w's can be in the range of 30° to 60°.

Angle $\omega'_4$ is enclosed by the exit surface 31' and the diffraction plane 360' of the second diffraction element 3', wherein $\omega'_4$ can be in the range of 30° to 60°.

Angle $\alpha'$ is enclosed by the second mirror 35' and the diffraction plane 360' of the second diffraction element 3'. An optional angular deviation from 45° of the angle $\alpha'$ is described by the angle $\beta'$.

Angle $\varepsilon'$ is enclosed by the second array detector 37', more precisely with the detection plane 370' of the second array detector 37' and the diffraction plane 360' of the second diffraction element 3'. An optional angular deviation from 45° is described here by the angle $\eta'$.

It should be noted, however, that it is advantageous, if a second holography arrangement 2' is comprised in the system 1, that the first entrance surface 31' of the second diffraction element 3' extends parallel to the second entrance surface 32 of the first diffraction element 3, so that the two entrance surfaces 32, 31' can be connected to one another, in particular without forming an air gap, so that the diffraction planes of the transmission diffraction grating arrangement 36, 36' of the first and second diffraction elements 3, 3' either run parallel to one another (cf., for example, FIG. 6) or enclose a 90° angle (not shown) with one another. In particular, it is provided that in an embodiment having two holography arrangements 2, 2', the first entrance surface 31' of the second diffraction element 3' and the second entrance surface 32 of the first diffraction element 3 each form an angle of 45° with the respective diffraction plane 360, 360', i.e. are perpendicular to the respective optical axis OA of the diffraction element 3, 3' (cf. FIG. 6).

The following is also noted regarding the laser light and the resulting reference light 100 and object light 200. The invention provides in particular that the laser light comprises a plurality of wavelengths. It is particularly advantageous if, in a wavelength range around the central wavelength 100-1, 100-2 or 200-1, 200-2, a plurality of separate spectral lines 106 or 206 (cf., for example, FIGS. 2 and 5), for example laser lines in the laser light, are comprised. A spectral line, for example, has a width in the range of up to 0.5 nm, preferably less than 0.1 nm. The wavelength range, in turn, may have a typical width of up to approximately 10 nm. The laser light and the transmission diffraction grating arrangement 36, 36' of the system 1 are in particular coordinated with one another. Since the transmission diffraction grating arrangement 36, 36' comprises at least one volume phase hologram grating, the following can first be noted. The volume phase hologram grating has a bandwidth around a central wavelength, ideally the central wavelength of the laser light, within which it sufficiently diffracts incident light in the Littrow configuration, wherein the central wavelength is diffracted "perfectly" by 2*45°=90°. Lasers having slightly different wavelengths around a central wavelength
are known as frequency comb lasers and can be produced
using quantum dot technology, for example. These are used,
for example, for frequency multiplexing of a broadband
transmission in telecommunications. Alternatively, it is also
conceivable that single-mode stripe lasers having slightly
different wavelengths are integrated close together on a laser
diode module and the output apertures are combined to form
a laser light source module via a specially integrated optical
chip. A fiber splitter could also become part of such a
module. Such a combination is possibly already conceivable
on the laser diode chip itself, which would simplify the
production process. To simplify matters, we can refer to a
laser light source having a central wavelength.

Multiple wavelengths around the central wavelength are
advantageous or even necessary in order to obtain clear
depth information about the phases of the individual wave-
length signals per object point or per illumination spot. The
lateral object information is generated from the hologram
frequencies, for example, by Fourier transformation. In
combination, a 3D object is recognized in principle, which
is known in principle to a person skilled in the art.

The following describes the advantageous properties of a
volume phase hologram grating in more detail:

When reference or object light is incident on the volume
phase hologram grating having the grating frequency $f_{gr}$, the
light having the central wavelength $\lambda_0$ is diffracted in the
Littrow arrangement by exactly 90° (=2*45°) in the direc-
tion of the prism surface 34, 34' or the exit surface 33, 33'
as already described. With slightly varying wavelengths
(multiple lines in the wavelength range of the laser light), the
following angular splitting $\Delta\theta$ results in this Littrow
arrangement:

$$\frac{\Delta\theta}{\Delta\lambda} = \frac{f_{gr}}{\cos(45°)} = \frac{2}{\lambda 0} \qquad \text{Eq. (1)}$$

At the central wavelength of 660 nm this is 3 mrad/nm
and at a central wavelength of 1300 nm this is 1.5 mrad/nm.
If a typical distance between two spectral lines is 200 μm,
the angle thus changes by $\Delta\theta$=0.6 mrad. If the wavelength
change is positive ($\lambda_0$+$\Delta\lambda$), the diffraction angle increases to
90°±$\Delta\theta$.

For object and reference light, the volume phase holo-
gram grating diffracts reference and object light in opposite
directions, thus providing twice the angle in relation to
equation (1), i.e. 2*$\Delta\theta$.

The advantage of the volume hologram in relation to a
solely planar grating lies in the selectivity regarding angle
and spectrum. Both properties are used in the manner
already described.

Considering the example above, 2*0.6 mrad=1.2 mrad
would therefore be estimated for a wavelength change of
200 pm. With typical resolution limits of 0.1 mrad per pixel
on the array detector, this means that there is at least a 10
pixel offset in relation to a neighboring spectral line having
the next higher/lower wavelength. The refractive index of
the prism arrangement increases the above angle again by
the factor $n_{prism}$ when exiting in the direction of the array
detector, since the beams are diffracted away from the
vertical. Since the refractive indices typically range between
1.5-1.9, a corresponding increase is to be expected.

From these considerations it becomes clear that the trans-
mission diffraction grating arrangement having a volume
phase hologram grating in Littrow configuration in the proposed prism arrangement already has particularly advan-
tageous properties for the spectral separation of a large
number of spectral lines. It is to be noted that the angular
splitting treated in Equation (1) comes only from the dis-
persion of the volume phase hologram grating and not from
the angle α or $\omega_2$.

The angle α or the angle $\omega_2$ causes the reference light
diffracted and reflected at the first mirror to be incident on
the transmission diffraction grating arrangement at an angle
in which the reference light is largely no longer diffracted (in
particular >70%) but propagates further in the direction of
the exit surface, thus providing a sufficiently high intensity
of reference light at the exit surface to form an interference
pattern with the object light. The corresponding beam course
is indicated schematically in FIG. 1. The same consider-
ations apply to a second holography arrangement of the
system.

For the following consideration, it is assumed for illus-
tration purposes that the first mirror 35 is arranged on the
prism surface 34 and thus the angles α and $\omega_2$ are identical.

In this case, the reference light of the central wavelength
$\lambda_0$ irradiated in Littrow configuration and reflected by the
first mirror is incident on the diffraction plane at an angle of
45°±2B and therefore has an angle of 2β with respect to the
diffracted object light. The wavelength-shifted proportion
$\lambda_0$±4% of the reflected reference light has an angle of
2$\Delta\theta$+2β with respect to the corresponding wavelength-
shifted proportion 2±$\Delta\lambda$ of the diffracted object light. The
different angles 2$\Delta\theta$ cause corresponding hologram frequen-
cies on the camera chip, which can be assigned to the
multiple wavelengths by Fourier transformation. The num-
ber of these wavelengths can be a minimum of two, but also
several dozen. Since modern camera chips can have several
thousand pixels per dimension, there are still enough spatial
frequencies (angles) free to be able to assign the lateral
image points in the object via the Fourier transformation,
which is known as such to a person skilled in the art. If the
array detector is spaced apart from the exit surface of the
diffraction element via an air gap, the angles are increased
once again by the factor of the refractive index of the prism
arrangement, as already explained above.

The inclination angle β can be derived approximately as
follows from the type of dispersion relationship of a volume
phase hologram grating having central wavelength $\lambda_0$, the
refractive index n (~1.5) of the grating, and the thickness D
of the volume phase hologram grating:

$$\delta_{FWHM} \approx \frac{n \lambda_0}{D} \qquad \text{Eq. (2)}$$

wherein $\delta_{FWHM}$ is the angle of incidence at which the
intensity of the diffracted light is only still approximately
50%. With a thickness of the volume phase hologram grating
of D=10 μm, a wavelength $\lambda_0$=660 nm, and a refractive
index n=1.5, an angle $\delta_{FWHM}$/2≈50 mrad results, according
to the definition of FWHM ("Full Width at Half Maxi-
mum"). Thus, the reference light reflected by the first mirror,
which is incident on the diffraction plane at an angle of 2β,
is to meet the condition, i.e. $\delta_{FWHM}$/2≈2β≈50 mrad, so that
half of the reference light propagates undiffracted through
the transmission diffraction grating arrangement, while the
other half is diffracted back in the direction of the first
entrance surface. However, since the reference light in
holography is always significantly stronger than the object beam, the attenuation of the reference beam by a factor of 2 does not represent a limitation.

The use of a volume phase hologram grating therefore has the further advantage that the object light within the FWHM is largely diffracted in the direction of the exit surface. This can also be achieved with a "classical" grating, but the reflected reference light would be largely diffracted away in the direction of the first entrance surface and would only be available with a weak signal strength for interference formation at the exit surface. Therefore, in this case, the diffraction efficiency of the diffraction grating would have to be reduced (for example to 50%), which in turn would result in an attenuation of the diffracted object light in the direction of the exit surface.

A further advantage of volume phase hologram gratings is that it is possible to create two volume phase hologram gratings having different central wavelengths arranged one inside the other, or alternatively to arrange two of these comparatively thin volume phase hologram grating structures on top of one another.

In FIGS. 2 to 6, some particularly advantageous embodiments of the optical system 1 are explained by way of example. Identical reference signs indicate the same elements, components, or features.

Figure 2:
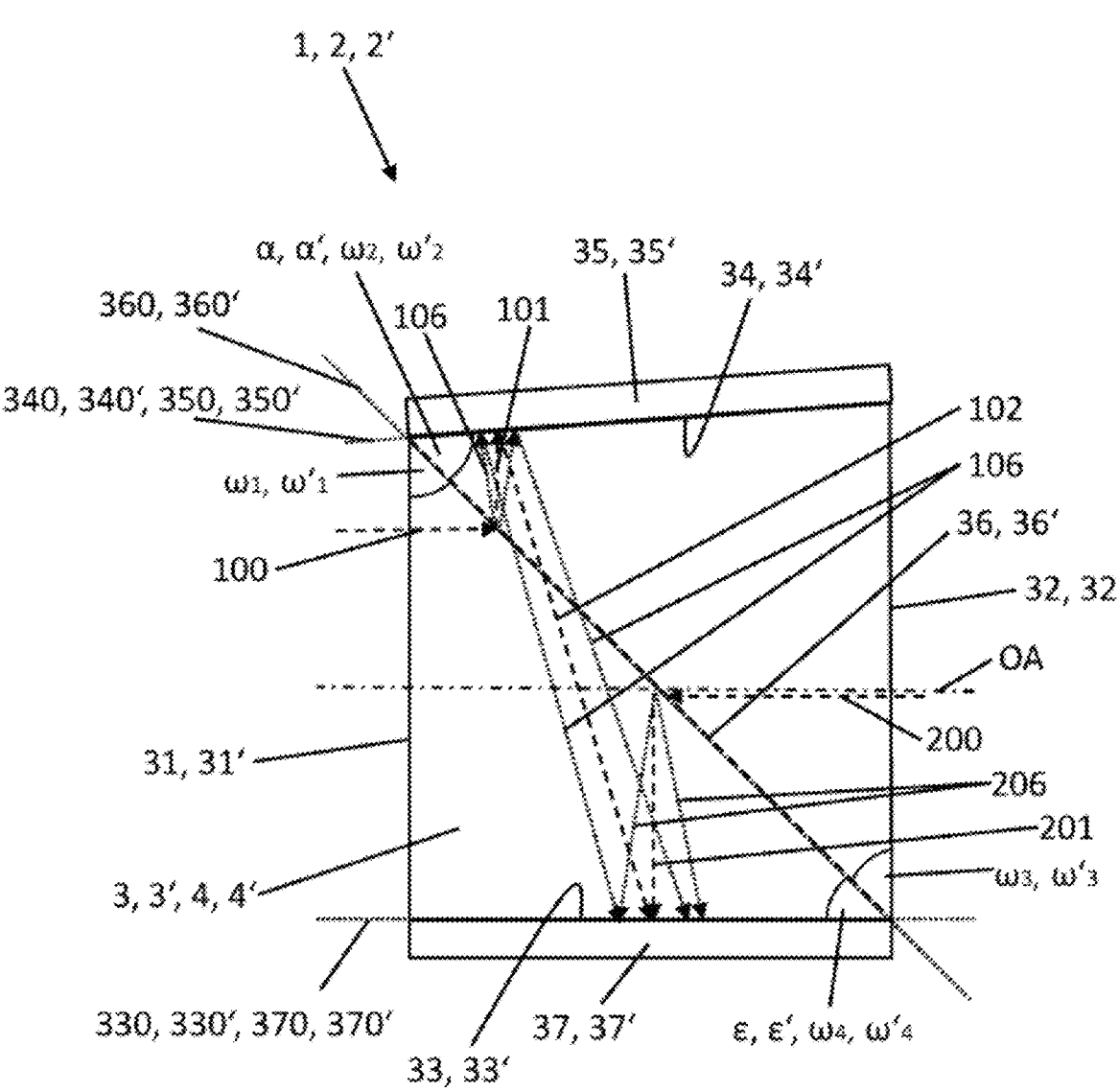
FIG. 2 shows a schematic sectional view of a second embodiment of the holography arrangement of the system according to the invention.

In FIG. 2, an advantageous embodiment of a first or second holography arrangement 2, 2″ according to the invention is shown.

Referring to the introduced angle relationships and reference signs, the angles $\omega_1$, $\omega_3$, $\omega_4$ (or, if it is a second diffraction element, the angles $\omega'_1$, $\omega'_3$, $\omega'_4$) of the diffraction element are 45°.

Furthermore, the angles $\omega_2$ and $\beta$ (or $\omega'_2$ and $\beta'$) are identical and the first or the second mirror 35, 35' is formed on the prism surface 34, 34' of the diffraction element 3, 3' in the form of a reflective layer. This has the advantage of creating a robust and compact optical system 1. Furthermore, this configuration of the first and second holography arrangements 2, 2' enables a serial arrangement in an optical system according to the invention (cf. FIG. 6), in which the first and second diffraction elements 3, 3' having the respective entrance surfaces 32, 31' can be arranged next to one another without an air gap.

The first or second array detector 37, 37' is also fixed directly on the exit surface 33, 33' of the diffraction element 3, 3', so that no air gap arises here either.

In particular, the prism arrangement 4, 4' in FIG. 2 can be formed in one piece or from two triangular prisms connected to one another along the diffraction plane 360, 360' via the transmission diffraction grating arrangement 36, 36'.

In FIG. 2, the beam path of the reference light in the diffraction element 3 or 3' is shown as an example for reference light, which comprises two further spectral lines 106 around a central wavelength, which form, for example, the edge values of the wavelength range around the central wavelength of the laser light 100, 200 and the volume phase hologram grating adapted thereto. Starting from reference light 100, the spectral lines are diffracted by the transmission diffraction grating arrangement 36 or 36' less or more than the central wavelength. Therefore, the beams of the spectral lines 106, after being diffracted by the transmission diffraction grating arrangement 36, 36', enclose an angle other than 45° with that of the diffraction plane. Due to the angular position a, $\alpha'$ of the mirror 35, 35', the reflected spectral lines diverge further from the beam 102 around the beam of the central wavelength 102 and are incident on the exit surface 33, 33' at laterally different locations.

The same applies to the object light 200, which is diffracted by the transmission diffraction grating arrangement 36, 36'. The spectral lines 206 of the laser light also result here in dispersive splitting of the object light 200 into spectral lines 206 diffracted to different degrees by the transmission diffraction grating arrangement 36, 36'.

Figure 3:
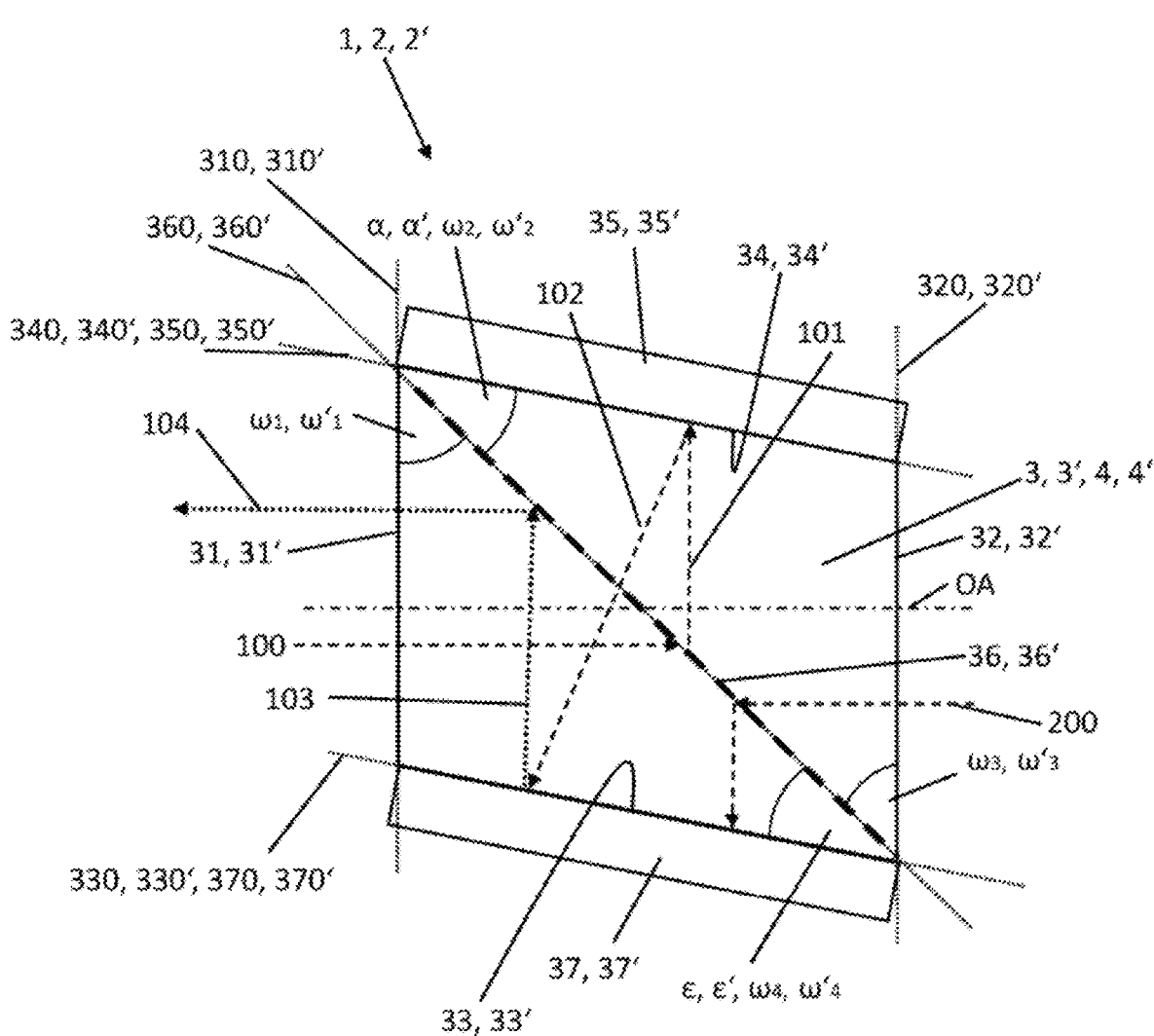
FIG. 3 shows a schematic sectional view of a third embodiment of the holography arrangement of the system according to the invention.

FIG. 3 shows a variant of the first or second holography arrangement 2, 2' of the optical system 1, in which the prism arrangement 4, 4' has a base surface in the form of a parallelogram, wherein the first and second entrance surface 31, 32 (or 31', 32') each enclose an angle $\omega_1$, $\omega_3$ (or $\omega'_1$, $\omega'_3$) of 45° with the diffraction plane 360, 360'—i.e. in particular are perpendicular to the optical axis OA of the diffraction element 3, 3', and the exit surface 33, 33' and the prism surface 34, 34' also run parallel, so that the angles $\omega_2$ and $\omega_4$ (or $\omega'_2$ and $\omega'_4$) are identical and less than 45°. Likewise, in this exemplary embodiment, the mirror 35, 35' is arranged directly (i.e. without forming a gap) on the prism surface 34, 34', so that the angle $\alpha$ is equal to the angle $\omega_2$ (and thus $\beta=\rho_2$) or the angle $\alpha'$ is equal to the angle $\omega'_2$ (and thus $\beta'=\rho'_2$). The mirror 35, 35' can in turn be designed as a reflective layer which has been vapor-deposited onto the prism surface 34, 34' using an appropriate method, for example.

In addition, the array detector 37, 37' is arranged directly on the exit surface 33, 33', so that the angles $\varepsilon$ and $\omega_4$ (or $\varepsilon'$ and $\omega'_4$) are also identical. This results in the following angle relations:

$$\alpha = \omega_2 = \omega_4 = \varepsilon < 45° \text{ or } \alpha' = \omega'_2 = \omega'_4 = \varepsilon' < 45° \text{ or,}$$

$$\alpha = \omega_2 = \omega_4 = \varepsilon > 45° \text{ or } \alpha' = \omega'_2 = \omega'_4 = \varepsilon' < 45°.$$

This embodiment is characterized by a simple geometry which simultaneously improves the suppression of interference signals (ghosting) on the array detector 37, 37', since, as indicated by the dotted arrows 103 and 104, light potentially reflected by the array detector 37, 37' due to the special angular relationships of the surfaces of the holography arrangement 2, 2', this light is again incident on the transmission diffraction grating arrangement 36, 36' at an angle of 45° and—with high diffraction efficiency—is diffracted again in the direction of the first entrance surface 31, 31' and thus guided out of the diffraction element 3, 3'.

Figure 4:
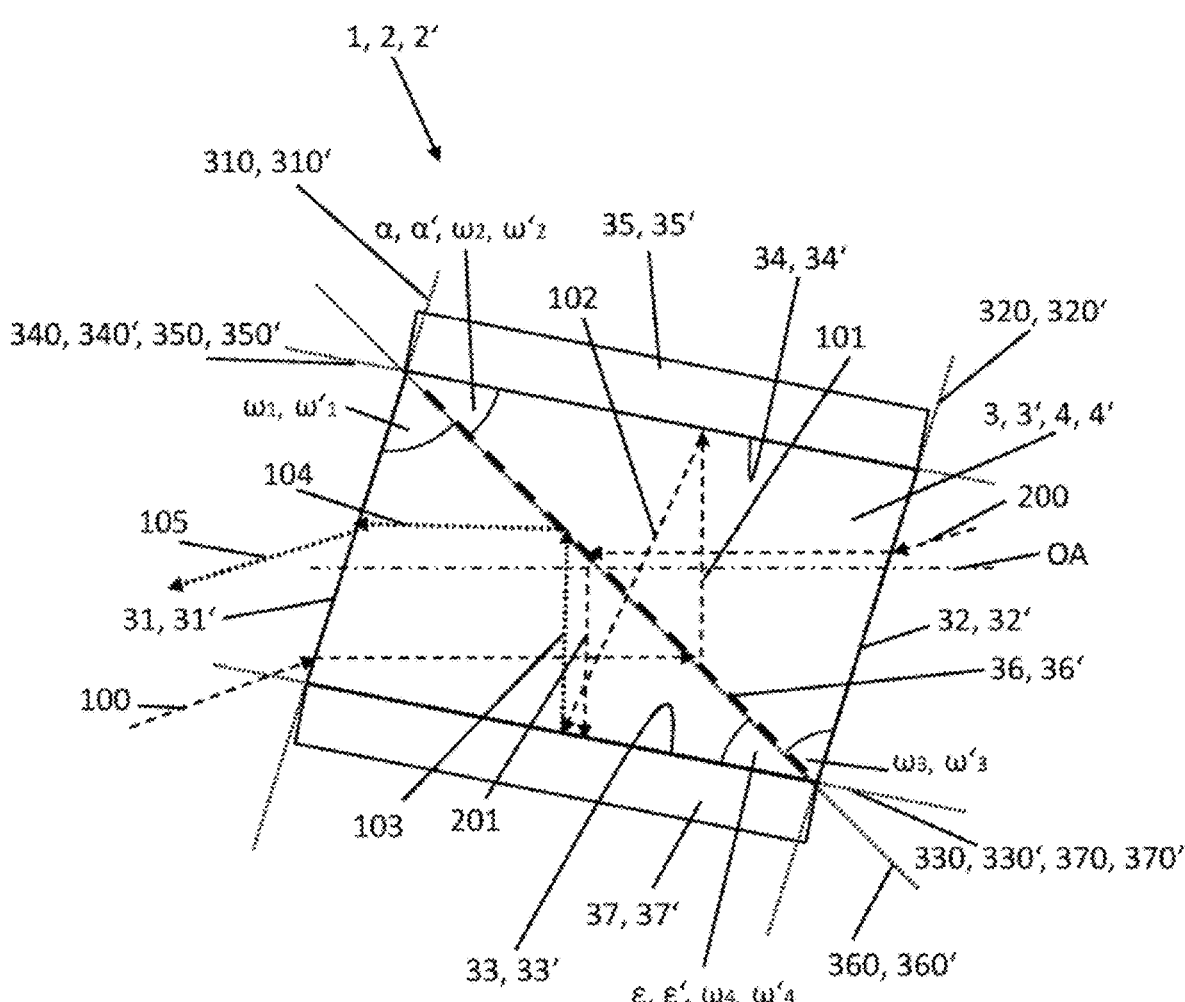
FIG. 4 shows a schematic sectional view of a fourth embodiment of the holography arrangement of the system according to the invention.

Similarly to FIG. 3, FIG. 4 shows an expanded variant of the first or second holography arrangement 2, 2″. The prism arrangement 4, 4' also has a parallelogram as its base surface, wherein, in contrast to FIG. 3, the angles of the first and second entrance surfaces $\omega_1$ and $\omega_3$ (or $\omega'_1$ and w's) are not equal to 45°. This ensures that the entrance surfaces 31, 32, (or 31', 32') do not extend perpendicular to the optical axis OA of the diffraction element 3, 3', which shows an advantageous deflection of the back reflections potentially occurring on these surfaces (see arrow 105).

It is to be noted that this geometry can also be used in a system 1 comprising two holography arrangements 2, 2' arranged in series by arranging the first entrance surface 31' of the second diffraction element 3' without an air gap on the second entrance surface 32 of the first diffraction element 3.

FIG. 5 shows an optical system 1 according to an embodiment of the invention, wherein in addition to the holography arrangement 2, 2' from the previous figures, further components of the system 1 are now also shown schematically.

First, the system in FIG. 5 comprises a laser light source 8 (dotted box) having only one laser 81, which is designed to provide laser light around a central wavelength and possibly with further spectral lines within a wavelength range. The laser light sources or lasers suitable for this purpose have already been disclosed as examples in previous paragraphs. The laser light source 8 can furthermore be configured to emit polarized laser light of a specific polarization. The laser light is then split into reference light 100 and object light 200 by means of a beam splitter. The splitting ratio can be unequal to 50:50, wherein preferably a larger proportion, for example 70% or 90% of the laser light, is allocated to the object light.

The beam splitter can be integrated in a fiber splitter 13, which is configured to couple the reference light 100 into a first polarization-maintaining single-mode fiber 10 and to couple the object light 200 into a second polarization-maintaining single-mode fiber 11. The first fiber 9 is arranged with one end in a focal point or at least in a focal plane of the collimation optical unit 5 of the optical system 1, so that reference light 100 is coupled out of the fiber 9, if necessary by means of a corresponding coupling lens or aperture 10, and the wavefront of the reference light is collimated by the collimation optical unit 5. The collimation optical unit 5 has an optical axis which, in the example of FIG. 5, extends co-linearly with the optical axis OA of the first diffraction element 3. If the first entrance surface 31 forms an angle not equal to 45° with the diffraction plane 360, then the optical axis of the collimation optics 5 is to be aligned accordingly so that the reference light propagates along the optical axis OA of the diffraction element 3 after entering the diffraction element 3. In this example, the optical axis of the collimation optical unit 5 is shifted parallel to the optical axis of the first diffraction element 3, so that reference light enters the diffraction element 3 in a region closer to the mirror and is thus superimposed on the corresponding beams 201, 206 of the object light at the array detector 37. The further course of propagation in the first holography arrangement 2 has already been discussed exhaustively and will not be repeated here.

The object light 200 propagates after the fiber splitter 13 along the second optical fiber 11 and is emitted by an imaging optical unit 12 at the end of the second fiber 11 in such a way that an intensity pattern is projected onto an object 300 to be measured.

The intensity pattern has at least one illumination spot on the object 300, but preferably many spots that are laterally separated from one another by non-illuminated regions of the pattern.

The object light 200 from the pattern reflected by the object 300 is captured by an objective lens 6 of the system 1 and, if it originates from the focal plane of the objective lens 6, is collimated and guided in the direction of the second entrance surface 32. There, the object light 200 enters the diffraction element 3 and is diffracted in the direction of the exit surface 33, where it is superimposed with the reference light 102. This superposition is recorded by the first array detector 37 and forwarded to a computer 400 for further processing, for example in the form of digital data. The computer 400 can reconstruct the wave field of the object light so that a 3D representation of the illuminated regions of the object can be generated.

The spots offset laterally in the intensity pattern have the result that each spot on the first array detector 37 can still be analyzed individually despite the spectral splitting on the array detector 37. In order to obtain complete information about the object, the object is to be scanned using the intensity pattern so that ideally every part of the object has been illuminated at least once with a spot and detected by the first array detector 37.

As already shown in FIG. 2, the beam path for the spectral lines 106 and 206 from the wavelength range around the central wavelength of the reference light beams 102 and object light beams 201 is also shown as an example in FIG. 5, which is advantageously determined by the dispersion properties of the transmission diffraction grating arrangement 36 or the volume phase hologram grating.

The holography arrangement shown in FIG. 5 can be replaced by another previously disclosed holography arrangement 2 without affecting the system 1, wherein the position and orientation of the collimation optical unit 5 and/or the objective lens 6 may need to be adjusted accordingly so that the system 1 assumes the Littrow configuration.

FIG. 6 shows an embodiment of the system 1 from FIG. 5 which, in contrast to the system in FIG. 5, comprises a first and a second holography arrangement 2, 2'. The first holography arrangement 2 comprises a first volume phase hologram grating 36 which is configured for a first central wavelength 100-1, 200-1, and the second holography arrangement 2' comprises a volume phase hologram grating 36' which is configured for a second central wavelength 100-2, 200-2. This means that the volume phase hologram grating 36 of the first diffraction element 3 diffracts the reference and object light around the first central wavelength 100-1, 200-1 in the Littrow configuration and allows light around the second central wavelength 100-2 to pass through undiffracted, while the volume phase hologram grating 36' of the second diffraction element 3' diffracts the reference and object light around the second central wavelength 100-2, 200-2 in the Littrow configuration and allows light around the first central wavelength 200-1 to pass through undiffracted. This allows an enlarged spectral range to be used for digital holography.

It is to be noted that in FIG. 6, for reasons of clarity, the beam paths of the spectral lines 106 and 206 around the respective central wavelengths 100-1, 100-2, 200-1, 200-2 are not shown.

In order to provide laser light having the two central wavelengths, the laser light source 8 comprises two lasers 81, 82, wherein a first laser 81 is configured to emit laser light around the first central wavelength 100-1, 200-1 (and in particular further spectral lines in a wavelength range around the first central wavelength), and wherein a second laser 82 is configured to emit laser light around the second central wavelength 100-2, 200-2 (and in particular further spectral lines in a wavelength range around the second central wavelength). The light of the two lasers 81, 82 is coupled into the first and second polarization-maintaining fibers 9, 11 by a fiber splitter 13, as already described in FIG. 5. If the bandwidth of the fibers 9, 11 is not sufficient to transport both central wavelengths single-mode, separate fibers can also be used for each central wavelength, which may be combined at their ends via a beam splitter or arranged slightly laterally offset before they are projected onto the object 300 via the imaging optical unit 12 or collimated via the collimation optical unit 5.

In the example of FIG. 6, the first and the second diffraction element 3, 3' are arranged in series and the second entrance surface 32 of the first diffraction element 3 is connected to the first entrance surface 31' of the second diffraction element 3' without an air gap, so that in particular a jump in the refractive index at the transition between the diffraction elements 3, 3' is avoided. For this purpose, the two entrance surfaces 31', 32 run parallel to one another.

Depending on the requirements, the first and second mirrors 35, 35' enclose the same or a different angle α, α' with the respective diffraction plane 360, 360'.

Each diffraction element 3,3' comprises its own array detector 37, 37', which may have an optical filter (not shown) connected upstream thereof to block stray light or reflections from wavelength ranges other than the intended one.

The signals recorded by the first and second array detectors 37, 37' at the respective exit surface 33, 33' are fed to the same computer 400, which can calculate a 3D representation of the object from the information.

The system 1 according to the invention makes it possible to enable digital holography in a compact and robust manner, for example in the minimally invasive medical field. The system is particularly configured and suitable to be included in an endoscope.

| List of reference signs | |
|---|---|
| 1 | optical system |
| 2 | first holography arrangement |
| 2' | second holography arrangement |
| 3 | first diffraction element |
| 3' | second diffraction element |
| 4 | first prism arrangement |
| 4' | second prism arrangement |
| 5 | collimation optical unit |
| 6 | objective lens |
| 8 | laser light source |
| 81, 82 | lasers |
| 9 | first optical fiber |
| 10 | input aperture |
| 11 | second optical fiber |
| 12 | imaging optical unit |
| 31, 31' | first entrance surface |
| 32, 32' | second entrance surface |
| 33, 33' | exit surface |
| 34, 34' | prism surface |
| 35 | first mirror |
| 36, 36' | transmission diffraction grating arrangement |
| 37 | first array detector |
| 37' | second array detector |
| OA | optical axis of the diffraction element |
| ω1 | angle between 310 and 360 |
| ω'1 | angle between 310' and 360' |
| ω2 | angle between 340 and 360 |
| ω'2 | angle between 340' and 360' |
| ω3 | angle between 320 and 360 |
| ω'3 | angle between 320' and 360' |
| ω4 | angle between 330 and 360 |
| ω'4 | angle between 330' and 360' |
| α | angle between 350 and 360 |
| α' | angle between 350' and 360' |
| ε | angle between 370 and 360 |
| ε' | angle between 370' and 360' |
| X | angle between 102 and 360 |
| 100 | reference light |
| 101 | diffracted reference light |
| 102 | reflected reference light |
| 103-105 | light reflections of reference light |
| 106 | spectral lines around central wavelength of reference light |
| 100-1 | first central wavelength of reference light |
| 100-2 | second central wavelength of reference light |
| 200 | object light |
| 201 | diffracted object light |
| 206 | spectral lines around central wavelength of object light |
| 200-1 | first central wavelength of object light |

-continued

| List of reference signs | |
|---|---|
| 200-2 | second central wavelength of object light |
| 300 | object |
| 400 | computer |

The invention claimed is:

1. An optical system (1) comprising at least the following components:

a first holography arrangement (2) comprising a first diffraction element (3) which is formed by a first prism arrangement (4) having at least a quadrangular base surface, wherein a lateral surface of the first prism arrangement (4) has the following lateral surface regions:

a) a first entry surface (31) for reference light (100) extending along a first entry plane (310), b) a second entry surface (32) for object light (200) extending along a second entry plane (320), wherein the first and second entry surfaces (31, 32) form opposite lateral surface regions of the first prism arrangement (4), c) an exit surface (33), which extends along an exit plane (330) and through which diffracted reference light (102) and diffracted object light (201) can exit from the first diffraction element 3), d) a prism surface (34) opposite to the exit surface (33), which extends along a prism plane (340), e) an optical transmission diffraction grating arrangement (36) arranged in the first diffraction element (3) and extending along a diffraction plane (360) which intersects the first entry plane (310) between the first entry surface (31) and the exit surface (33), wherein the transmission diffraction grating arrangement (36) of the first diffraction element (3) comprises at least a first volume phase hologram grating, and in that the first holography arrangement (2) has a first mirror (35) with a first mirror plane (350) on the side of the prism surface (34), wherein the first mirror plane (350) encloses an angle α with the diffraction plane (360) and the prism plane (340) encloses an angle 02 with the diffraction plane (360), wherein at least one of the angles α, W2 is different from 45°, wherein the system (1) comprises a first array detector (37), comprising a two-dimensional array of detector elements, wherein the first array detector (37) is configured to detect light exiting from the exit surface (33) of the first diffraction element (3) wherein the first array detector (37) is arranged on the exit surface (33) of the first diffraction element (3).

2. The optical system (1) according to claim 1, wherein the base surface of the first prism arrangement (4) is a parallelogram, a rectangle, or a square.

3. The optical system (1) according to claim 1, wherein the first mirror (37) is arranged or formed on the prism surface (33) of the first diffraction element (3).

4. The optical system (1) according to claim 1, wherein the optical transmission diffraction grating arrangement (36) of the first holography arrangement comprises a second volume phase hologram grating, wherein the first and the second volume phase hologram gratings have different central wavelengths.

5. The optical system (1) according to claim 1, comprising a second holography arrangement (2') having a second diffraction element (3'), which is formed by a second prism arrangement (4') with at least a quadrangular base surface, wherein the first holography arrangement (2) and the second holography arrangement (2') are arranged next to one another along an optical axis (OA) of the first diffraction element (3), and a lateral surface of the second prism arrangement (4') has the following lateral surface regions:

f) a first entry surface (31') for reference light (100) extending along a first entry plane (310'), g) a entry entrance surface (32') for object light (200) extending along a second entry plane (320'), wherein the first and second entry surfaces (31', 32') form opposite lateral surface regions of the second prism arrangement (4'), h) an exit surface (33'), which extends along an exit plane (330') and through which diffracted reference light (102) and diffracted object light (201) can exit from the second diffraction element (3'), i) a prism surface (33') opposite to the exit surface (33'), which extends along a prism plane (330'), j) an optical transmission diffraction grating arrangement (36') arranged in the second diffraction element (3') and extending along a diffraction plane (360') which intersects the first entry plane (310') between the first entry surface (31') and the exit surface (33') of the second diffraction element (3'), wherein the transmission diffraction grating arrangement (36') of the second diffraction element (3') comprises at least a first volume phase hologram grating, and in that the second holography arrangement (2') has a second mirror (35') with a second mirror plane (350') on the side of the prism plane (340'), wherein the second mirror plane (350') encloses an angle $\alpha'$ with the diffraction plane (360') and the prism plane (340') encloses an angle $\omega'_2$ with the diffraction plane (360'), wherein at least one of the angles $\alpha'$, $\omega'_2$ is different from 45°.

6. The optical system (1) according to claim 5, wherein the second entry surface (32) of the first diffraction element (3) is connected to the first entry surface (31') of the second diffraction element (3').

7. The optical system (1) according to claim 1, wherein the optical system (1) has, on the side of the first entry surface (31) of the first diffraction element (3), a collimator (5) for reference light (100), which has an optical axis which runs in the direction of the first entry surface (31) of the first diffraction element (3), and wherein the collimator (5) is configured to collimate reference light (100) before it enters through the first entry surface (31) of the first diffraction element (3).

8. The optical system according to claim 6, wherein the first diffraction element (3) is formed integrally with the first entry surface (31') of the second diffraction element (3') along its second entry surface (32), or wherein the second entry surface (32) of the first diffraction element (3) is adhesively bonded or welded to the first entry surface (31') of the second diffraction element (3').

9. The optical system (1) according to claim 1, wherein the optical system (1) comprises an objective lens (6) for object light (200), wherein the objective lens (6) is arranged in the optical system (1) such that object light (200) propagating from the objective lens (6) in the direction of the second entry surface (32) of the first diffraction element (3) and/or in the direction of the second entry surface (32') of the second diffraction element (3') is collimated when the object light (200) radiates in and/or near a focal plane of the objective lens (6) in the direction of the objective lens (6).

10. The optical system (1) according to claim 1, characterized in that the optical system (1) comprises the following components:

a laser light source (8) configured to provide laser light having one or more central wavelengths, at least one first optical fiber (9), which is configured to guide the laser light of the laser light source (8) to an input aperture (10) of the collimator (5), so that the collimator (5) guides the collimated laser light in the form of reference light (100) to the first holography arrangement (2), at least one second optical fiber (11) which is configured to guide the laser light of the laser light source (8) to an output aperture (12) of the optical system (1), from which an object (300) to be detected is to be illuminated using laser light in the form of object light (200).

11. The optical system (1) according to claim 10, characterized in that the optical system (1) comprises a fiber splitter (13), which is designed to split the laser light of the laser light source (8) and to couple it into the first optical fiber (9) and second optical fibers (11).

12. The optical system (1) according to claim 1, characterized in that the optical system (1) has an imaging optical unit (12) which is designed to project object light (200), in the form of an intensity pattern onto an object (300) to be detected, wherein the intensity pattern consists of at least one illuminated region or wherein the intensity pattern consists of a plurality of disjoint illuminated regions.

13. The optical system (1) according to claim 1, characterized in that the optical system (1) is designed to provide laser light which comprises wavelengths from at least two wavelength ranges, wherein a first wavelength range is arranged around a first central wavelength and comprises wavelengths in particular in the form of spectral lines which lie outside a second wavelength range, wherein the second wavelength range is arranged around a second central wavelength and comprises wavelengths in particular in the form of spectral lines.

14. An optical system (1) comprising at least the following components: a first holography arrangement (2) comprising a first diffraction element (3) which is formed by a first prism arrangement (4) having at least a quadrangular base surface, wherein a lateral surface of the first prism arrangement (4) has the following lateral surface regions:

a) a first entry surface (31) for reference light (100) extending along a first entry plane (310), b) a second entry surface (32) for object light (200) extending along a second entry plane (320), wherein the first and second entry surfaces (31, 32) form opposite lateral surface regions of the first prism arrangement (4), c) an exit surface (33), which extends along an exit plane (330) and through which diffracted reference light (102) and diffracted object light (201) can exit from the first diffraction element (3), d) a prism surface (34) opposite to the exit surface (33), which extends along a prism plane (340), e) an optical transmission diffraction grating arrangement (36) arranged in the first diffraction element (3) and extending along a diffraction plane (360) which intersects the first entry plane (310) between the first entry surface (31) and the exit surface (33), wherein the transmission diffraction grating arrangement (36) of the first diffraction element (3) comprises at least a first volume phase hologram grating, and in that the first holography arrangement (2) has a first mirror (35) with a first mirror plane (350) on the side of the prism surface (34), wherein the first mirror plane (350) encloses an angle α with the diffraction plane (360) and the prism plane (340) encloses an angle 02 with the diffraction plane (360), wherein at least one of the angles α, w2 is different from 45°, wherein the system further comprises a second holography arrangement (2') having a second diffraction element (3'), which is formed by a second prism arrangement (4') with at least a quadrangular base surface, wherein the first holography arrangement (2) and the second holography arrangement (2') are arranged next to one another along an optical axis (OA) of the first diffraction element (3), and a lateral surface of the second prism arrangement (4') has the following lateral surface regions:

f) a first entry surface (31') for reference light (100) extending along a first entry plane (310'), g) a entry entrance surface (32') for object light (200) extending along a second entry plane (320'), wherein the first and second entry surfaces (31', 32') form opposite lateral surface regions of the second prism arrangement (4'), h) an exit surface (33'), which extends along an exit plane (330') and through which diffracted reference light (102) and diffracted object light (201) can exit from the second diffraction element (3'), i) a prism surface (33') opposite to the exit surface (33'), which extends along a prism plane (330'), j) an optical transmission diffraction grating arrangement (36') arranged in the second diffraction element (3') and extending along a diffraction plane (360') which intersects the first entry plane (310') between the first entry surface (31') and the exit surface (33') of the second diffraction element (3'), wherein the transmission diffraction grating arrangement (36') of the second diffraction element (3') comprises at least a first volume phase hologram grating, and in that the second holography arrangement (2') has a second mirror (35') with a second mirror plane (350') on the side of the prism plane (340'), wherein the second mirror plane (350') encloses an angle α' with the diffraction plane (360') and the prism plane (340') encloses an angle w'2 with the diffraction plane (360'), wherein at least one of the angles α', is different from 45°, wherein the system (1) comprises a first array detector (37), comprising a two-dimensional array of detector elements, wherein the first array detector (37) is configured to detect light exiting from the exit surface (33) of the first diffraction element (3) wherein the first array detector (37) is arranged on the exit surface (33) of the first diffraction element (3).

15. An optical system (1) comprising at least the following components: a first holography arrangement (2) comprising a first diffraction element (3) which is formed by a first prism arrangement (4) having at least a quadrangular base surface, wherein a lateral surface of the first prism arrangement (4) has the following lateral surface regions:

a) a first entry surface (31) for reference light (100) extending along a first entry plane (310), b) a second entry surface (32) for object light (200) extending along a second entry plane (320), wherein the first and second entry surfaces (31, 32) form opposite lateral surface regions of the first prism arrangement (4), c) an exit surface (33), which extends along an exit plane (330) and through which diffracted reference light (102) and diffracted object light (201) can exit from the first diffraction element (3), d) a prism surface (34) opposite to the exit surface (33), which extends along a prism plane (340), e) an optical transmission diffraction grating arrangement (36) arranged in the first diffraction element (3) and extending along a diffraction plane (360) which intersects the first entry plane (310) between the first entry surface (31) and the exit surface (33), wherein the transmission diffraction grating arrangement (36) of the first diffraction element (3) comprises at least a first volume phase hologram grating, and in that the first holography arrangement (2) has a first mirror (35) with a first mirror plane (350) on the side of the prism surface (34), wherein the first mirror plane (350) encloses an angle α with the diffraction plane (360) and the prism plane (340) encloses an angle W2 with the diffraction plane (360), wherein at least one of the angles α, w2 is different from 45°, wherein the optical system (1) has an imaging optical unit (12) which is designed to project object light (200) in the form of an intensity pattern onto an object (300) to be detected, wherein the intensity pattern consists of at least one illuminated region or wherein the intensity pattern consists a plurality of disjoint illuminated regions, wherein the system (1) comprises a first array detector (37), comprising a two-dimensional array of detector elements, wherein the first array detector (37) is configured to detect light exiting from the exit surface (33) of the first diffraction element (3) wherein the first array detector (37) is arranged on the exit surface (33) of the first diffraction element (3).

\* \* \* \* \*